United States Patent
Quake et al.

(10) Patent No.: US 9,909,180 B2
(45) Date of Patent: Mar. 6, 2018

(54) MEASUREMENT AND COMPARISON OF IMMUNE DIVERSITY BY HIGH-THROUGHPUT SEQUENCING

(71) Applicant: The Board of Trustees of the Leland Stanford Junior University, Palo Alto, CA (US)

(72) Inventors: Stephen R. Quake, Stanford, CA (US); Joshua Weinstein, Stanford, CA (US); Ning Jiang, Stanford, CA (US); Daniel S. Fisher, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 431 days.

(21) Appl. No.: 14/172,642

(22) Filed: Feb. 4, 2014

(65) Prior Publication Data

US 2014/0235478 A1 Aug. 21, 2014

Related U.S. Application Data

(60) Provisional application No. 61/760,459, filed on Feb. 4, 2013.

(51) Int. Cl.
C12Q 1/68 (2006.01)

(52) U.S. Cl.
CPC ..... *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 7,785,783 B2 | 8/2010 | Morley et al. |
| 8,236,503 B2 | 8/2012 | Faham et al. |
| 8,507,205 B2 | 8/2013 | Faham et al. |
| 8,628,927 B2 | 1/2014 | Faham et al. |
| 8,691,510 B2 | 4/2014 | Faham et al. |
| 8,748,103 B2 | 6/2014 | Faham et al. |
| 8,795,970 B2 | 8/2014 | Faham et al. |
| 2006/0046258 A1 | 3/2006 | Lapidus et al. |
| 2006/0259248 A1 | 11/2006 | Collette et al. |
| 2007/0072240 A1 | 3/2007 | Brekke et al. |
| 2007/0161001 A1 | 7/2007 | Leshkowitz |
| 2008/0166718 A1 | 7/2008 | Lim et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2012/0058902 A1 | 3/2012 | Livingston et al. |
| 2012/0183969 A1 | 7/2012 | Han |
| 2013/0065768 A1 | 3/2013 | Zheng et al. |
| 2013/0150252 A1 | 6/2013 | Faham et al. |
| 2013/0196328 A1 | 8/2013 | Pepin et al. |
| 2013/0202718 A1 | 8/2013 | Pepin et al. |
| 2013/0236895 A1 | 9/2013 | Faham et al. |
| 2013/0324422 A1 | 12/2013 | Faham et al. |
| 2014/0255929 A1 | 9/2014 | Zheng |
| 2014/0255944 A1 | 9/2014 | Carlton et al. |
| 2014/0315725 A1 | 10/2014 | Faham et al. |

FOREIGN PATENT DOCUMENTS

| | | |
|---|---|---|
| EP | 1 544 308 B1 | 6/2005 |
| EP | 2 364 368 B1 | 9/2011 |
| WO | 2003/044225 A2 | 5/2003 |
| WO | 2008/147879 A1 | 12/2008 |
| WO | 2009/137255 A2 | 11/2009 |
| WO | 2010/053587 A2 | 5/2010 |
| WO | 2011/140433 | 11/2011 |
| WO | 2011/140433 A1 | 11/2011 |

OTHER PUBLICATIONS

Ademokun; et al., "Vaccination-introduced changes in human B-cell repertoire and pneumococcal IgM and IgA antibody at different ages", Aging Cell (2011), 10(6):922-30.

Michaeli; et al., "Automated cleaning and pre-processing of immunoglobulin gene sequences from high-throughput sequencing", Frontiers in Immunology (Dec. 2012), 3:386, 16 pgs.

Boyd et al., "Measurement and clinical monitoring of human lymphocyte clonality by massively parallel VDJ pyrosequencing", Sci Transl Med (2009), 1(12):12ra23.

Lim et al., "The IgE repertoire in PBMCs of atopic patients is characterized by individual rearrangements without variable region of the heavy immunoglobulin chain bias", J Allergy Clin Immunol (2007),120(3):696-706.

Weinstein et al., "High-throughput sequencing of the zebrafish antibody repertoire", Science (2009), 324(5928):807-10.

Altin et al., (1997), "The role of CD45 and Cd-45 associated molecules in T cell activation," *Immunol. Cell Biol.*, vol. 75, No. 5, pp. 430-445.

Arnaout, RA., (Oct. 28, 2005) "Specificity and overlap in gene segment-defined antibody," *BMC Genomics*, vol. 28, No. 6, p. 148, 9 pages total.

ATCC, "Jurkat, Clone E6-1 (ATCC TIB-152)," located at http://www.atcc.org/Products/All/TIB-152.aspx#characteristics, 1 page, Jun. 5, 2015.

Boyd, Scott D. et al., Measurement of Human Lymphocyte Clonality by Massively Parallel VDJ Pyrosequencing, Science Translational Medicine, vol. 1, No. 12, Dec. 23, 2009, pp. 1-30.

Campbell, (2008), "Subclonal phylogenetic structures in cancer revealed by ultra-deep sequencing," *PNAS*, vol. 105 No. 35, pp. 13081-13086.

(Continued)

*Primary Examiner* — James Martinell
(74) *Attorney, Agent, or Firm* — Pamela J. Sherwood; Bozicevic, Field & Francis LLP

(57) ABSTRACT

High-throughput long read sequencing is used to perform immunogenomic characterization of expressed antibody repertoires in the context of vaccination. Informatic analysis allows global characterizations of isotype distributions, determination of the lineage structure of the repertoire and measure age and antigen related mutational activity. Global analysis of the immune system's clonal structure provides direct insight into the effects of vaccination and provides a detailed molecular portrait of age-related effects.

8 Claims, 25 Drawing Sheets
(10 of 25 Drawing Sheet(s) Filed in Color)

(56) References Cited

OTHER PUBLICATIONS

Curran et al., (2004), "Nucleotide Sequencing of Psoriatic Arthritis Tissue before and during Methotrexate Administration Reveals a Complex Inflammatory T Cell Infiltrate with Very Few Clones Exhibiting Features That Suggest They Drive the Inflammatory Process by Recognizing Autoantigens," *The Journal of Immunology*, vol. 172, No. 3, pp. 1935-1944.

Damle et al., (2002), "B-cell chronic lymphocytic leukemia cells express a surface membrane phenotype of activated, antigen-experienced B lymphocytes," *Blood*, vol. 99, No. 11, pp. 4087-4093.

Diluvio et al., (2006), "Identical TCR beta-chain rearrangements in streptococcal angina and skin lesions of patients with psoriasis vulgaris" *J. Immunol.* vol. 176, No. 11, pp. 7104-7111.

Dressman et al., (2003), "Transforming single DNA molecules into fluorescent magnetic particles for detection and enumeration of genetic variations," *PNAS*, vol. 100. No. 15, pp. 8817-8822.

Delassus, S. et al. "PCR-based analysis of the murine immunoglobulin heavy-chain repertoire," Journal of Immunological Methods, Aug. 18, 1995, vol. 184, No. 2, pp. 219-229.

Freeman et al., (2009, published online Jun. 18, 2009), "Profiling the T-cell receptor beta-chain repertoire by massively parallel sequencing," *Genome Research*, vol. 19, pp. 1817-1824.

Furmanski et al., (Jan. 2008), "Public T cell receptor beta-chains are not advantaged during positive selection," *J Immunol.*, vol. 180, pp. 1029-1039.

Glanville et al., (Dec. 1, 2009, published online Oct. 29, 2009), "Precise determination of the diversity of a combinatorial antibody library gives insight into the human immunoglobulin repertoire," *PNAS*, vol. 106, No. 48, pp. 20216-20221.

Han et al., (2009), "Immunorepertoire analysis by multiplex PCR amplification and high throughput sequencing," (Abstract) *J. Immunol.*, p. 182, (Meeting Abstract Supplement) 42.6.

Heyer et al., (1999), "Exploring Expression Data: Identification and Analysis of Coexpressed Genes" Genome Res. vol. 9, pp. 1106-1115.

Holtmeier, W. et al. "IgA and IgM V(H) repertoires in human colon: evidence for clonally expanded B cells that are widely disseminated," Gastroenterology, Nov. 2000, vol. 119, No. 5, pp. 1253-1266.

Kita et al., (1998), "T Cell Receptor Clonotypes in Skin Lesions from Patients with Systemic Lupus Erythematosus," *The Journal of Investigative Dermatology*, vol. 110, pp. 41-46.

Mardis, (Sep. 2008, published online Jun. 2008), "Next-generation DNA sequencing methods," *Annu. Rev. Genomics Hum. Genet.*, vol. 9, pp. 387-402.

Miceli et al., (1991), "The roles of CD4 and CD8 in T cell activation," *Semin. Immunol.*, vol. 3, No. 3., pp. 133-141, abstract only.

Opposition of EP Patent No. 2364368 filed on Oct. 14, 2014 by Boxall IPM Ltd., 24 pages.

Opposition of EP Patent No. 2364368 filed on Oct. 14, 2014 by Dr. Christian Mueller, 44 pages.

Robbins et al., (Nov. 5, 2009, published online Aug. 2009), "Comprehensive assessment of T-cell receptor β-chain diversity in αβ T cells," *Blood*, vol. 114, No. 19, pp. 4099-4107.

Shendure et al., (Oct. 9, 2008), "Next-generation DNA sequencing," *Nature Biotechnology*, vol. 26, pp. 1135-1145.

Shendure et al., (May 2004) "Advanced Sequencing Technologies: Methods and Goals," *Nat. Rev. Genet.*, vol. 5, No. 5, pp. 335-344.

Skulina et al., (2004, published online Feb. 24, 2004), "Multiple sclerosis: Brain-infiltrating CD8+ T cells persist as clonal expansions in the cerebrospinal fluid and blood," *PNAS*,vol. 100, No. 8, pp. 2428-2433.

Stanley, (2002), "Chapter 7, T Cells," *Essentials of Immunology & Serology*, Delman, Thomson Learning, p. 95.

Striebich et al., (Oct. 15, 1998) "Selective Accumulation of Related CD4+ T Cell Clones in the Synovial Fluid of Patients with Rheumatoid Arthritis," *J. Imm.*, vol. 161, pp. 4428-4436.

Universite de Liege, (Oct. 10, 2014), "Roche 454 FLX Technology: how it works," located at http://www.giga.ulg.ac.be/jcms/cdu_15721/fr/roche-454-flx-technology-how-it-works, 2 pages.

U.S. Appl. No. 61/045,586, filed Apr. 16, 2008 by Jian Han, 39 pages.

VanderBorght et al., (2002) "Dynamic T cell receptor clonotype changes in synovial tissue of patients with early rheumatoid arthritis: effects of treatment with cyclosporin A (Neoral)," *J. Rheumatol.*, vol. 29, No. 3, pp. 416-426.

Wang et al., (2007), "HIV integration site selection: Analysis by massively parallel pyrosequencing reveals association with epigenetic modifications," *Genome Res.*, vol. 17, No. 8, pp. 1186-1194.

Wang et al., (2009), "Immunorepertoire analysis by multiplex PCR amplification and high throughput sequencing," (Poster—Program 42.6), *The 96th Annual Meeting of the American Association of Immunologists*, Seattle, Washington, May 8-12, 2009.

Wang et al., (Jan. 26, 2010). "High throughput sequencing reveals a complex pattern of dynamic interrelationships among human T cell subsets," *PNAS*, vol. 107, No. 4, pp. 1518-1523.

Warren et al., (2009), "Profiling model T-cell metagenomes with short reads," *Bioinformatics*, vol. 25, No. 4, pp. 458-464.

Warren et al., (2011, published online Feb. 24, 2011), "Exhaustive T-cell repertoire sequencing of human peripheral blood samples reveals signatures of antigen selection and a directly measured repertoire size of at least 1 million clonotypes," *Genome Research*, vol. 27, pp. 790-797.

Weinstein et al. (May 8, 2009), "Supporting Online Material for 'High-throughput sequencing of the zebrafish antibody repertoire'," *Science*, vol. 324, available at www.sciencemag.org/cgi/content/full/324/5928/807/DC1.

White, H.N., "Restriction-PCR fingerprinting of the immunoglobulin VH repertoire: direct detection of an immune response and global analysis of B cell clonality," European Journal of Immunology, Oct. 1998, vol. 28, No. 10, pp. 3268-3279.

Wu, Y.-C. et al., "High-throughput immunoglobulin repertoire analysis distinguishes between human IgM memory and switched memory B-cell populations," Blood, Aug. 19, 2010, vol. 116, No. 7, pp. 1070-1078.

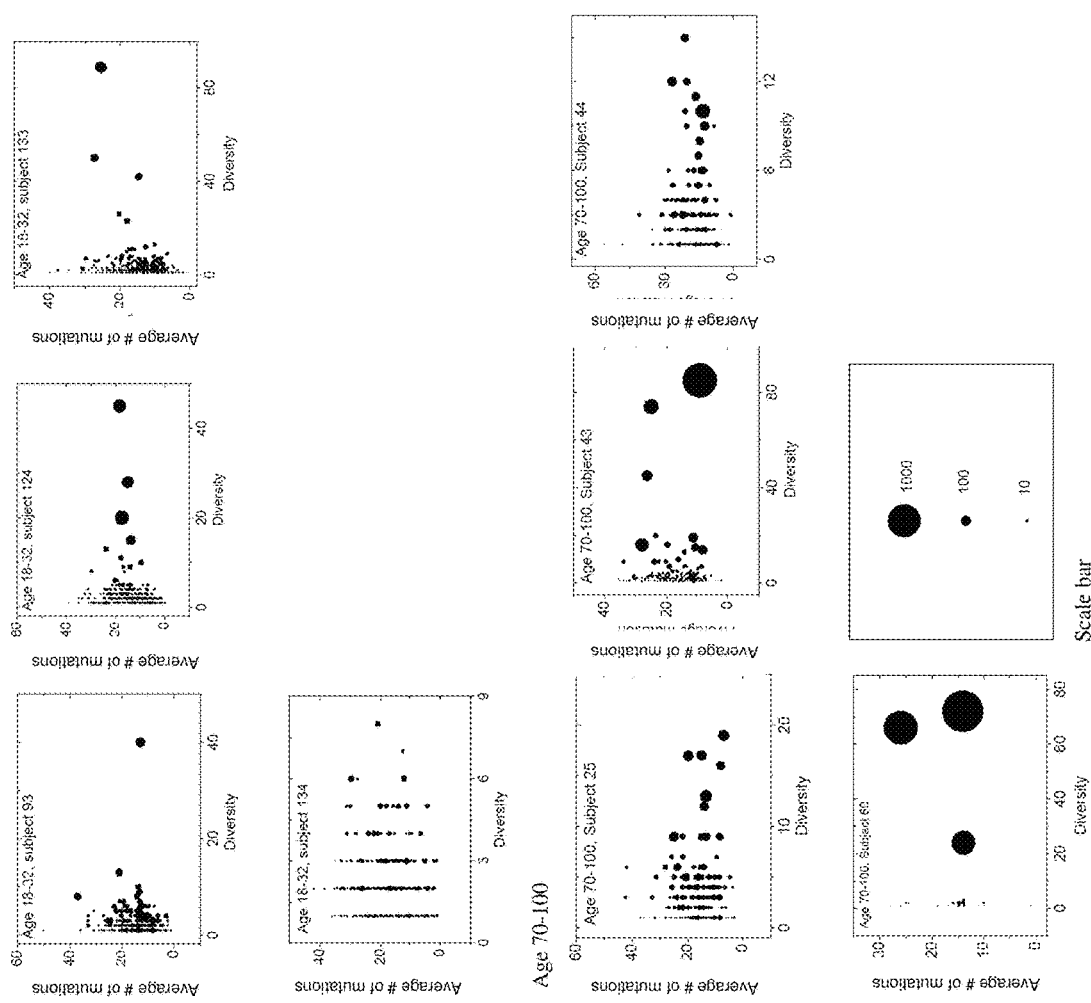

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 1
cgcagaccct ctcactcac                                              19

<210> SEQ ID NO 2
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 2
tggagctgag gtgaagaagc                                             20

<210> SEQ ID NO 3
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 3
tgcaatctgg gtctgagttg                                             20

<210> SEQ ID NO 4
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 4
ggctcaggac tggtgaagc                                              19

<210> SEQ ID NO 5
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 5
tggagcagag gtgaaaaagc                                             20

<210> SEQ ID NO 6
<211> LENGTH: 19
<212> TYPE: DNA
<213> ORGANISM: Artificial sequence
```

```
<220> FEATURE:
<223> OTHER INFORMATION: Synthetic nucleic acid sequence

<400> SEQUENCE: 6
ggtgcagctg ttggagtct                                                    19

<210> SEQ ID NO 7
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 7
actgttgaag ccttcggaga                                                   20

<210> SEQ ID NO 8
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 8
aaacccacac agaccctcac                                                   20

<210> SEQ ID NO 9
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 9
agtctggggc tgaggtgaag                                                   20

<210> SEQ ID NO 10
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 10
ggcccaggac tggtgaag                                                     18

<210> SEQ ID NO 11
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 11
ggtgcagctg gtggagtc                                                     18

<210> SEQ ID NO 12
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 12
aagaccgatg ggcccttg                                                     18
```

<210> SEQ ID NO 13
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 13
gaagaccttg gggctggt                                              18

<210> SEQ ID NO 14
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 14
gggaattctc acaggagacg                                            20

<210> SEQ ID NO 15
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 15
gaagacggat gggctctgt                                             19

<210> SEQ ID NO 16
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 16
gggtgtctgc accctgata                                             19

<210> SEQ ID NO 17
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 17
gggaagtagt ccttgaccag                                            20

<210> SEQ ID NO 18
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 18
ggggaagaag ccctggac                                              18

<210> SEQ ID NO 19
<211> LENGTH: 18
<212> TYPE: DNA
<213> ORGANISM: Artificial sequence
<220> FEATURE:
<223> OTHER INFORMATION: Synthetic nucleic acid sequence

```
<400> SEQUENCE: 19
ggccacgctg ctcgtatc                                                  18

<210> SEQ ID NO 20
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 20
agggaatgtt tttgcagcag                                                20

<210> SEQ ID NO 21
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 21
ccacagggct gttatccttt                                                20

<210> SEQ ID NO 22
<211> LENGTH: 215
<212> TYPE: DNA
<213> ORGANISM: Artificial sequence
<220> FEATURE:
<223> OTHER INFORMATION: Synthetic nucleic acid sequence

<400> SEQUENCE: 22
ctcagctatt agtggtagtg gtggtagcac atactacgca gactccgtga agggccggtt    60
caccatctcc agagacaatt ccaagaacac gctgtatctg caaatgaaca gcctgagagc   120
cgaggacacg gccgtatatt actgtgcgaa accccaaat acggtgtacc cctttgacta    180
ctggggccag ggaaccctgg tcaccgtctc ctcag                              215

<210> SEQ ID NO 23
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 23

Ala Thr Asp Arg Val Thr Ala Gly Tyr Ser Ser Gly Trp Tyr His Pro
1               5                   10                  15

Leu Asp Tyr
```

MEASUREMENT AND COMPARISON OF IMMUNE DIVERSITY BY HIGH-THROUGHPUT SEQUENCING

CROSS REFERENCE TO RELATED APPLICATIONS

This application claims priority from U.S. Provisional Application Ser. No. 61/760,459, filed Feb. 4, 2013, which is incorporated by reference herein in its entirety for all purposes.

BACKGROUND OF THE INVENTION

A feature of the adaptive immune response is the ability to generate a wide diversity of binding molecules, e.g. T cell antigen receptors and antibodies. A variety of molecular mechanisms exist to generate initial diversity, including genetic recombination at multiple sites. Armed with this initial repertoire of binding moieties, naïve B and T cells circulate where they can come in contact with antigen. Upon exposure to antigen there can be a positive selection process, where cells expressing immunological receptors having desired binding properties are expanded, and may undergo further sequence modification, for example somatic hypermutation, and additional recombination. There can also be a negative selection process, where cells expressing immunological receptors having undesirable binding properties, such as self-reactivity, are deleted. As a result of these selective processes, the repertoire of binding specificities in an individual sample can provide a history of past antigenic exposures, as well as being informative of inherent repertoire capabilities and limitations.

Adaptive immunological receptors of interest include immunoglobulins, or antibodies. This repertoire is highly plastic and can be directed to create antibodies with broad chemical diversity and high selectivity. There is also a good understanding of the potential diversity available and the mechanistic aspects of how this diversity is generated. Antibodies are composed of two types of chains (heavy and light), each containing a highly diversified antigen-binding domain (variable). The V, D, and J gene segments of the antibody heavy-chain variable genes go through a series of recombination events to generate a new heavy-chain gene. Antibodies are formed by a mixture of recombination among gene segments, sequence diversification at the junctions of these segments, and point mutations throughout the gene. The mechanisms are reviewed, for example in Maizels (2005) Annu. Revu. Genet. 39:23-46; Jones and Gellert (2004) Immunol. Rev. 200:233-248; Winter and Gearhart (1998) Immunol. Rev. 162:89-98.

Another adaptive immunological receptor of interest is the T cell antigen receptor (TCR), which is a heterodimer of two chains, each of which is a member of the immunoglobulin superfamily, possessing an N-terminal variable (V) domain, and a C terminal constant domain. The variable domain of the TCR α-chain and β-chain has three hypervariable or complementarity determining regions (CDRs). The β-chain has an additional area of hypervariability (HV4) that does not normally contact antigen. Processes for generating diversity of the TCR are similar to those described for immunoglobulins. The TCR alpha chain is generated by VJ recombination, while the beta chain is generated by V(D)J recombination. Similarly, generation of the TCR gamma chain involves VJ recombination, while generation of the TCR delta chain occurs by V(D)J recombination. The intersection of these specific regions (V and J for the alpha or gamma chain, V D and J for the beta or delta chain) corresponds to the CDR3 region that is important for antigen-MHC recognition. It is the unique combination of the segments at this region, along with palindromic and random N- and P-nucleotide additions, which accounts for the TCR binding repertoire.

While reference is made to binding specificities, and indeed a good deal of serological analysis is based on the physical interactions between antigen and receptor, the underlying cause of the diversity lies in the genetic sequences expressed by lymphocytes, which sequences reflect the myriad processes of recombination, mutation and selection that have acted on the cell. Estimates of immune diversity for antibodies or the related T cell receptors either have attempted to extrapolate from small samples to entire systems or have been limited by coarse resolution of immune receptor genes. However, certain very elementary questions have remained open more than a half-century after being posed: It is still unclear what fraction of the potential repertoire is expressed in an individual at any point in time and how similar repertoires are between individuals who have lived in similar environments. Moreover, because each individual's immune system is an independent experiment in evolution by natural selection, these questions about repertoire similarity also inform our understanding of evolutionary diversity and convergence.

Methods of precisely determining the immune receptor repertoire of an individual, or a sample of interest from an individual, are of great interest for prognosis, diagnosis, and characterization. The present invention addresses that issue.

SUMMARY OF THE INVENTION

Methods and compositions are provided for using nucleic acid sequence analysis to measure characteristics and function of the immune response to vaccination. A principal application of the invention is in measuring the immunological diversity present in a biological sample in response to administration of a vaccine. Biological samples may be obtained following vaccination, and may further be compared to biological samples from time points before vaccine administration, or at multiple time points following vaccine administration. The response may be used in the selection of candidate vaccines; to determine the responsiveness of individuals to candidate vaccines, and the like. By determining the underlying genetics of the immune repertoire, one can better characterize immune response, immune history, and immune competency. Those characterizations, in turn, lead to improved diagnostic, prognostic, and therapeutic outcomes. Finally, methods of the invention allow personalized immune profiling.

The samples from which immunological-receptor encoding nucleic acids are obtained are typically complex and include, among others, blood, lymph, and biopsy samples. Such samples typically comprise greater than $10^3$ or more different sequences for a receptor of interest. The biological sample may be chosen based upon a particular organ or system, condition or disease of interest. In some embodiments the sample comprises immune-related cells, such as lymphocytes, e.g. T cells, B cells, natural killer cells, etc. Immunological receptor molecules of interest include immunoglobulins, T cell antigen receptors, and major histocompatibility receptors, or fragments thereof. The nature of sequence variations in the sample can be recorded and displayed in an informative manner, e.g. represented in a tree, represented in a three dimensional plot, etc. The analysis of sequence variation is useful for predictive and diagnostic methods relating to the immune capabilities and history of an individual. Such predictions and diagnoses can be used to guide clinical decisions.

Any appropriate sequencing method may be used in the context of the invention. Common methods include sequencing-by-synthesis, Sanger or gel-based sequencing, sequencing-by-hybridization, sequencing-by-ligation, or any other available method. Particularly preferred are high throughput sequencing methods, preferably without the need for cloning or functional expression of the targeted immune molecules. In some embodiments, all the cells in the sample are treated as a single sample, i.e. without segregation or sorting, and used as a source of nucleic adds for sequencing. In other embodiments, cells of interest, including cells of the adaptive immune system, e.g. B cells expressing a marker of interest, plasmablasts, T cells expressing a marker of interest, and the like, are sorted from the starting sample population and used as a source of nucleic adds for sequencing. In some embodiments the sorting is by positive selection, while in others, the sorting is performed by negative selection.

The sequencing data are statistically analyzed to compute correlations in the repertoire (or sets of immunological receptors) of different samples, where samples may be obtained from different individuals or from a single individual at different times, different sites of the body, synthetic libraries, etc. Time points may be taken, for example, following exposure to an antigenic challenge, such as a vaccine, in response to a candidate therapy, during a transplantation process, and the like.

The information obtained from the immune repertoire analysis may be used to diagnose a condition, to monitor treatment, to select or modify therapeutic regimens, and to optimize therapy. With this approach, therapeutic and/or diagnostic regimens can be individualized and tailored according to the specificity data obtained at different times over the course of treatment, thereby providing a regimen that is individually appropriate. In addition, patient samples can be obtained at any point during the treatment process for analysis.

Methods of statistical analysis include the use of algorithms to correct for bias introduced in sample preparation and sequencing of immune repertoires. An algorithm, for example using clustering and PCR filter, may be used to correct for sequence errors (or amplification bias) introduced during sample preparation and sequencing of immune repertoires. Algorithms are provided for the assignment of immune repertoire sequences into V, D, J, and C classes. Algorithms are provided for the assignment of immune repertoire sequences to individual heavy chains, light chains, CDR3, T-cell receptor alpha, beta, delta or gamma chains, etc.

The total corrected repertoire (or set of immunological receptors) can be used to determine the heterogeneity of an immune repertoire (or set of immunological receptors) by computing the entropy. The total corrected repertoire can be characterized by computing the frequency distributions of VDJC/antibody heavy chains.

The invention includes suitable sets of primers for obtaining high throughput sequence information for immunological molecules of interest, e.g. immunoglobulin sequence information, T cell receptor sequence information, MHC sequence information, etc. Sequencing can be performed on sets of nucleic adds across many individuals or on multiple loci in a sample obtained from one individual. Sequence analysis is performed on nucleic add obtained from cells present in the sample of interest, which may be genomic DNA or a portion thereof, cDNA, or portion thereof; or may be mRNA or cDNA obtained therefrom. In some embodiments cDNA is preferred. Where cDNA is analyzed, the methods may include the use of gene specific primers for reverse transcription of the immunological receptor sequences of interest.

Analysis may include amplifying cDNA using a set of primers designed to selectively bind immunological receptor gene sequences. For example, primers may be designed to amplify functional V gene segments of immunoglobulin loci, to amplify functional V gene segments of TCR loci, to amplify immunoglobulin or TCR constant region segments, to amplify consensus MHC gene segments, and the like. In some embodiments, an independent primer set is included to test PCR bias.

The present disclosure also provides a method for diagnosis or prognosis of a condition of interest, comprising: obtaining one or more reference samples comprising cells of interest; performing an immune repertoire analysis on the reference sample(s); using clustering analysis on the immune repertoire analysis results to identify features common to the condition of interest; performing immune repertoire analysis on a test sample obtained from an individual in need of diagnosis; comparing the repertoire analysis results obtained from the test sample to reference repertoire analysis results, wherein a pre-determined level of similarity to reference repertoire analysis results are indicative of the absence or presence of the condition.

Conditions of interest for diagnosis and prognosis include numerous aspects of Immune competence and antigenic exposure, e.g. including the absence or presence of autoimmune disease or predisposition to autoimmune disease; the status of transplantation; the presence of cancers of the immune system, e.g. leukemias, lymphomas, myelomas, etc.; exposure to antigenic stimulus, e.g. exposure to cancer antigens; exposure to viral, bacterial, parasitic antigens; exposure to vaccines; exposure to allergens; exposure to foodstuffs, e.g. gluten proteins, etc.; the innate repertoire of an individual indicating an inherent ability to respond to an antigen of interest; and the like.

Yet another method provided herein is a method for screening for a therapeutic agent comprising: exposing a first subject to one or more test agents; obtaining a suitable cell sample from the subject, e.g. a blood sample, etc.; performing immune repertoire analysis on said cell sample; and comparing the immune repertoire analysis results to a immune repertoire analysis result derived from either: (i) a second reference sample with a known response profile; or (ii) the first subject prior to said exposing step; and identifying an agent that affects immune repertoire in a desirable manner, e.g. deletion of self-reactive receptors; enhancement of pathogen-specific receptors; etc. The subject may be, for example, suffering or susceptible to an autoimmune disease, a chronic infection, following transplantation of a tissue, suffering from a cancer, etc. A therapeutic agent can be an antibody or antibody fragment, a drug or other small molecule, nucleic add (for example an siRNA), RNA, DNA, RNA-DNA chimera, protein, peptide, and the like.

Further provided herein is a method of determining likelihood of a response by a subject to an agent, which may include a therapeutic agent, an infectious agent, a vaccine, an autoantigen, and the like, comprising; obtaining a suitable cell sample from the subject, e.g. a blood sample, etc.; performing immune repertoire analysis on said cell sample; and comparing the immune repertoire analysis results to a immune repertoire analysis result derived from a reference sample with a known response profile to said agent; and determining likelihood of a response by a subject based on immune repertoire.

Also provided herein is a method of collecting data regarding an immune repertoire, comprising the steps of: collecting data regarding a immune repertoire using any of the methods described herein and sending said data to a computer. A computer can be connected to a sequencing apparatus. Data corresponding to an immune repertoire can further be stored after sending, for example the data can be stored on a computer-readable medium which can be extracted from the computer. Data can be transmitted from the computer to a remote location, for example, via the internet.

The present disclosure also provides methods of characterizing a set of immunological receptors, or fragments thereof, comprising: a) sequencing a population of nucleic adds encoding at least $10^3$, $10^4$, $10^5$, $10^6$, $10^7$, $10^8$, $10^9$, $10^{10}$, $10^{11}$, $10^{12}$ or more immunological receptors, or fragments thereof, or obtaining at least $10^3$, $10^4$, $10^5$, $10^6$, $10^7$, $10^8$, $10^9$, $10^{10}$, $10^{11}$, $10^{12}$ or more sequencing reads from a cellular sample; and b) using sequencing data from step a) to characterize said set of immunological receptors. Some embodiments also comprise applying a statistical metric that characterizes diversity or a clustering analysis to the sequencing data from step a) in order to characterize said set of immunological receptors or fragments thereof. In some cases, sequence variation is represented as a function of sequence frequency. In some cases, the statistical metric used is an entropy metric, an ecology metric, a variation of abundance metric, a species richness metric, or a species heterogeneity metric.

Also provided herein are methods of comparing a set of immunological receptors from an organism with a set of immunological receptors from another organism or from a reference sample. In some cases, (1) immunological receptors from an organism are compared to a reference sample; (2) immunological receptors from a second organism are compared to a reference sample; and the results of (1) are compare to those from (2).

Further provided herein are methods of selecting a treatment for a person afflicted with a condition comprising: a) sequencing a population of nucleic adds encoding immunological receptors or fragments thereof of said person; b) using sequence data from step a to characterize said person's immunological response; and c) selecting a treatment based on said characterization. In some embodiments, the method comprises a method of diagnosing a person suspected of having a condition comprising: a) sequencing a population of nucleic adds encoding immunological receptors, or fragments thereof, of said person; b) using sequence data from step a to characterize said person's immunological response; and c) selecting a treatment or diagnosis based on said characterization.

Also provided herein are software products tangibly embodied in a machine-readable medium, the software product comprising instructions operable to cause one or more data processing apparatus to perform operations comprising: a) clustering sequence data from a plurality of immunological receptors or fragments thereof; and b) providing a statistical analysis output on said sequence data. Also provided herein are software products tangibly embodied in a machine-readable medium, the software product comprising instructions operable to cause one or more data processing apparatus to perform operations comprising: storing sequence data for more than $10^3$, $10^4$, $10^5$, $10^6$, $10^7$, $10^8$, $10^9$, $10^{10}$, $10^{11}$, $10^{12}$ immunological receptors or more than $10^3$, $10^4$, $10^5$, $10^6$, $10^7$, $10^8$, $10^9$, $10^{10}$, $10^{11}$, $10^{12}$ sequence reads.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3B and 3C, respectively, from the main text with twin status indicated by arrows. p value was calculated by Mann-Whitney U test.

DETAILED DESCRIPTION

Figure 1:
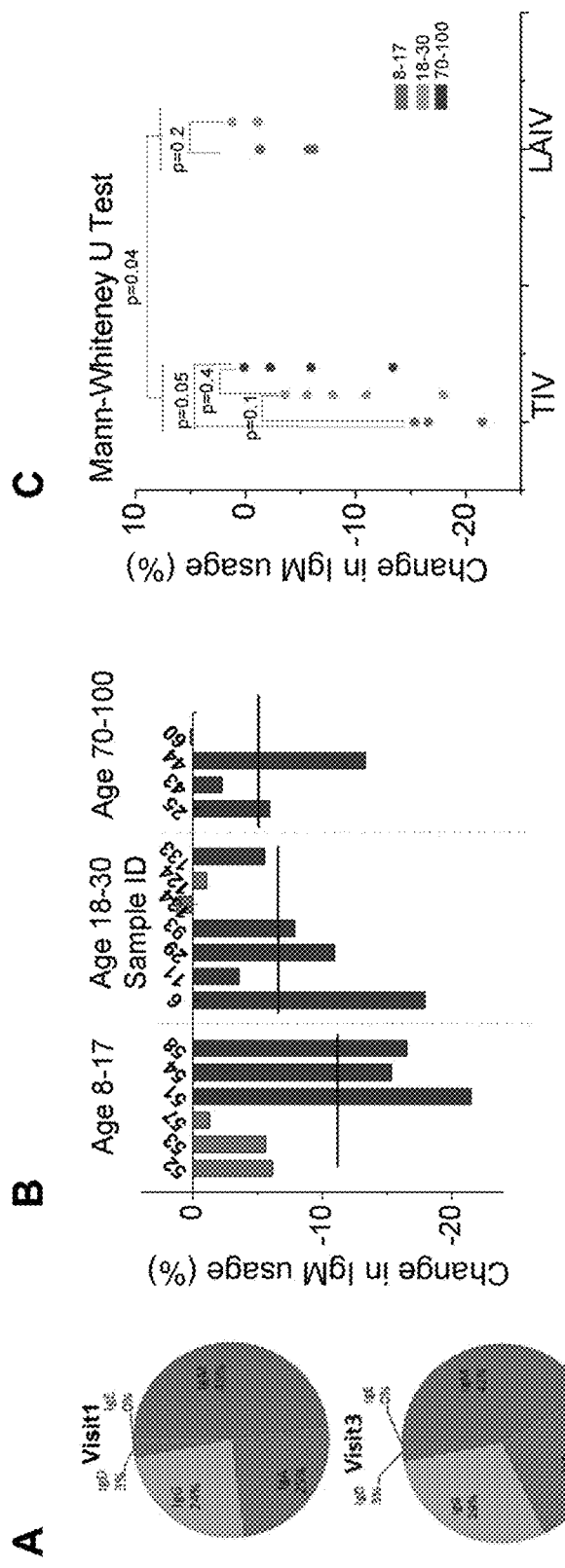
FIG. 1. Antibody isotype distribution changes after vaccination. (A), antibody isotype composition in PBMCs at visit 1 (before vaccination, top) and visit 3 (28±4 days after vaccination, bottom) averaged for all subjects. (B), percent change of individual's relative IgM usage in PBMCs from visit 1 to visit 3. The subject IDs were labeled on horizontal axis. (C), comparison of relative change in IgM in different age group and vaccine types. p value was calculated by Mann-Whitney U test (3 samples for TIV receivers of age 8-17, 5 samples for TIV receivers of age 18-32, 4 samples for TIV receivers of age 70-100, 3 samples for LAIV receivers of age 8-17 and 2 samples for LAIV receivers of age 18-32). Red, LAIV receivers; blue, TIV receirvers. Percent change=(IgM reads in visit 1/total reads in visit 1)−(IgM reads in visit 3/total reads in visit 3).

Methods and compositions are provided for sequence analysis of the immune repertoire. Analysis of sequence information underlying the immune repertoire provides a significant improvement in understanding the status and function of the immune system. For example, sequence information is useful to diagnose disease, immune status, prognosis, and response to therapy. Sequencing is also useful in therapeutic selection and monitoring and in the evaluation of therapeutic candidates.

The invention involves obtaining nucleic add from a biological sample and sequencing DNA or RNA relating to immunological receptor molecules. Sequencing information obtained from an individual sample is then compared to known sequences (e.g., in a database), to sequences from other samples, or to sequences from the same source over time.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Immune Repertoire Analysis or Analysis of Sets of Immunological Receptors

Methods of the invention allow characterization of the immune repertoire by sequencing all or a portion of the molecules that make up the immune system, including, but not limited to immunoglobulins, T cell receptors, and MHC receptors. Samples may represent all or a part of the immune repertoire of the individual from which the sample is obtained. As described above, any biological sample is complex in terms of the number of immune receptor sequences that are present. Methods of the invention contemplate high-throughput sequence of the complex array of immune-encoding nucleic acids present in a biological sample. Samples may also be processed to produce a library of nucleic acids (e.g., DNA, RNA, cDNA, mRNA, cRNA) encoding immunological receptors. The library may comprise genomic DNA or RNA or may be a synthetic library created by any method known in the art, including from in vitro random mutagenesis of nucleic acids.

The cells in a sample for analysis may have been separated or enriched prior to analysis, or a sample, e.g. a clinical sample, may be analyzed in the absence of any enrichment.

To obtain the sequence information, the cells present in the sample are lysed and nucleic acids of interest (e.g., genomic DNA, mRNA, cDNA, cRNA, etc.) are collected. Where mRNA is being analyzed, it will generally be converted to cDNA by reverse transcriptase. Primers for cDNA synthesis, as described above, may be selective for the immunological receptor of interest. The immune receptor sequences are then amplified with a set of primers selective for the immunological receptor of interest.

During PCR amplification there is a possibility of introducing a bias, and thus it may be desirable to include a control amplification, and an analysis step to normalize the data. The degree of PCR bias introduced in the sample preparation and sequencing process can be estimated by comparing the representation of the known clones before and after PCR, and determining the bias that is introduced. In the quantitative analyses that follow, these measured biases are used to normalize the data. The control data may also be used to measure sequencing errors. Other methods of controlling for amplification bias include one or more of the following methods (described in more detail herein and in the examples): PCR filter, clustering analysis, and using two or more primer sets.

The amplified pool (or, in some cases, a pool that has not been amplified) of nucleic acids is then subjected to high throughput sequencing (e.g., massively-parallel sequencing). In some embodiments of the invention, the analysis uses pyrosequencing (e.g., massively parallel pyrosequencing) relying on the detection of pyrophosphate release on nucleotide incorporation, rather than chain termination with dideoxynucleotides, and as described by, for example, Ronaghi of al. (1998) Science 281:363; and Ronaghi et al. (1996) Analytical Biochemistry 242:84, herein specifically incorporated by reference. The pyrosequencing method is based on detecting the activity of DNA polymerase with another chemiluminescent enzyme. Essentially, the method allows sequencing of a single strand of DNA by synthesizing the complementary strand along it, one base pair at a time, and detected which base was actually added at each step. The template DNA is immobile and solutions of selected nucleotides are sequentially added and removed. Light is produced only when the nucleotide solution complements the first unpaired base of the template.

Sequencing platforms that can be used in the present disclosure include but are not limited to: pyrosequencing, sequencing-by-synthesis, single-molecule sequencing, nanopore sequencing, sequencing-by-ligation, or sequencing-by-hybridization. Preferred sequencing platforms are those commercially available from Illumina (RNA-Seq) and Helicos (Digital Gene Expression or "DGE"). "Next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina as described U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

The effects of sequencing error or amplification error can be mitigated by the clustering process that allows one to determine a consensus sequence by grouping several reads together, and thus average out the error. The clustering algorithm may be tested on the control data in order to validate parameter choices.

The high throughput sequencing provides a very large dataset, which is then analyzed in order to establish the repertoire. Non-limiting examples of data analysis steps are summarized in the flow chart of FIG. 12.

Grouping identical sequences and preliminary V/J determination: initially sequences may be matched based on perfect identity, and the number of identical reads stored. Quality scores of identical reads are then averaged. V- and J-reference genome sequences (or synthetic reference sequences) are Smith-Waterman aligned to each sequence. (Other reference sequences that could be used are any combination of V-, D-, J- and C-). To avoid edge effects (due to enzymatic trimming) the reference-genome alignment five base-pairs away from the edges of the alignment are given higher weight. Those sequences failing to match minimally to any reference gene segment are discarded. Those that are ambiguous (matching equally to more than one reference genome segment) are retained but are recorded in an output file for being ambiguous (their provisional V-assignment is given to the first enumerated V-segment in the ambiguous subset).

Sequence subsets grouped in V/J combinations where V-segments are sufficiently similar: After preliminary V/J assignments, genomic-V sequences are aligned to one another, and genomic clusters are formed based on single-linkage clustering with a threshold (e.g., 6 bp-distance threshold). Sequences grouped under V/J combinations with V's belonging to the same cluster are grouped for pairwise alignment.

Pairwise alignment: Pair-wise alignment of sequences can be achieved with a specific algorithm, e.g., a quality-score-weighted Smith-Waterman algorithm. With the start positions of the alignment fixed (due to common reverse primers), the alignment grid is confined to the area less than or equal to a specific number of base pairs (e.g., 9 bp) off the diagonal (effectively limiting the number of admissible gap-errors or deletion-errors to 9 on a single read length).

Pairwise distance matrices: Matrices such as Smith-Waterman distance matrices for each V/J grouping can be outputted to text files for later reference.

Subsampling/rarefaction: Pre-determined sampling depths can be used to randomly select reads across all V/J combinations. Using printed distance matrices, sub-matrices are assembled and used for clustering.

Clustering and consensus determination: Seeded quality-threshold clustering is performed by seeding clusters with the sequence i that maximizes the centrality measure $c_i = \Sigma_j \exp(-d_{ij})$ where $d_{ij}$ is the alignment distance between i and all sequences j. Clustering then proceeds by adding to the cluster whichever sequence minimally increases the diameter of the cluster (ie the maximum distance between any two members). Once no sequence can be added without increasing the diameter above a defined threshold, cluster-formation terminates. Consensus sequences for each cluster are determined by sequence-vote: if there is a sequence with the most identical reads corresponding to it, that sequence is made the consensus. Otherwise the consensus is assigned the sequence that maximizes the centrality measure, above, relative to all other members of the same cluster.

Lineage analysis: After identical sequences have been grouped (with read-number/abundance stored), sequences containing stop-codons, ambiguous bases, or gaps relative to the reference genome are discarded. Junctional regions (the end of the V-encoded region to the beginning of the J-encoded region) are determined by using a moving window, whose size is equal to its distance from the end of the genomic exon, to find the furthest location from the end of each junction at which sequence-identity dropped below 50%. The junctional boundary is then defined as the furthest occurrence of a mismatch/insertion/deletion within the window (see Example 1)

Any two sequences with junction boundaries varying by at most one nucleotide and having greater than or equal to 80% identity at the VOJ junction are allowed to form single-linkage clusters. These clusters allow sequences to "chain", so that multiple sequences that differ in increments from one another can be traced back to the original un-mutated sequence. Sequences retain their identity, but the clusters they form defined hypothetical lineages. Whichever member sequence has the fewest differences relative to the reference genome (away from the junction as illustrated above) is defined as the naïve sequence of the lineage. Mutations are determined by direct comparison to this sequence. Similar methods can be used to determine V, D, J, C, VJ, VDJ, VJC, VDJC lineage usage or diversity.

Final VDJ assignment: For clustered sequences, the consensus is aligned to V and J segments as in the preliminary assignments (or C-, D-segments as appropriate). The junctions derived using the same algorithm as above are then aligned to all possible D-segments, with a high gap-open penalty (to prevent the alignment from being significantly affected by non-templated nucleotides). Similar methods can be applied to determine final V, D, J, C, VJ, VDJ, VJC, VDJC assignments.

Diversity determination, rarefaction, PCR filter: Control measurements show clustered 250 bp read-length sequences having 90% of their reads correctly clustered, roughly what is expected for PCR error rates of 5e-5 per base pair per cycle for an effective number of cycles numbering between 20 and 30. Rarefaction controls show clustering correctly accounting for all sequences without PCR, suggesting that "orphan" sequences can be treated as PCR errors alone. This is corroborated by the fact that for PCR-amplified controls, applying the PCR filter with a 90%-of-reads criterion is exactly the point at which diversity counts are allowed to saturate as a function of sequencing depth. Clusters are added to the correct-cluster pool, starting with the most abundant, and adding clusters in decreasing abundance until the top 90% of reads are included, at which point the algorithm terminates. This is done for each V/J (or any other V/J/D/C, etc.) combination independently to avoid bias.

A rough estimate for total diversity, T, can be derived from knowing the distribution of unique sequences, Prob(x), over all abundance x $$r_i = \frac{\sum_{x_i=x} \left(1 - \left(1 - x\left(T\sum_j x_j Prob(x_j)\right)^{-1}\right)^M\right)^2 Prob(x)}{\sum_{x_i=x} \left(1 - \left(1 - x\left(T\sum_j x_j Prob(x_j)\right)^{-1}\right)^M\right) Prob(x)}$$

VDJ lineage diversity: VDJ usage is enumerated by the number of observed lineages falling into each VJ, VDJ, VJC, or VDJC (e.g., VDJ) combination at a given read-depth.

VDJ and unique sequence abundance histograms: Histograms are plotted by binning VDJ and unique sequence abundances (the latter which is either clustered or has undergone lineage-analysis filtering and grouping) into log-spaced bins.

3D representation of VJ, VDJ, VJC, or VDJC (e.g., VDJ) usage: Repertoires are represented by applying V-, D-, J-, and/or C-segments to different axes on a three-dimensional plot. Using either abundance (generally read number, which can be bias-normalized) or observed lineage diversity, bubbles of varying sizes are used at each V/D/J/C coordinate to represent the total usage of that combination.

Mutation vs. sequence abundance plots: After undergoing lineage analysis, unique sequences are binned by read-number (or bias-normalized abundance) into log-spaced bins. For a given abundance-bin, the number of mutations per unique sequence is averaged, giving a mutation vs. abundance curve.

Correlative measures of V, D, J, C, VJ, VDJ, VJC, VDJC, antibody heavy chain, antibody light chain, CDR3, or T-cell receptor) usage (Pearson, KL divergence): VDJ, VJC, or VDJC (e.g., VDJ) combinations are treated as vectors with indexed components $v_i$, weighted by either lineage-diversity or abundance for that VDJ combination. Pearson correlations and KL-divergences between each pair of individuals are then calculated over the indices i.

The results of the analysis may be referred to herein as an immune repertoire analysis result, which may be represented as a dataset that includes sequence information, representation of V, D, J, C, VJ, VDJ, VJC, VDJC, antibody heavy chain, antibody light chain, CDR3, or T-cell receptor usage, representation for abundance of V, D, J, C, VJ, VDJ, VJC, VDJC, antibody heavy chain, antibody light chain, CDR3, or T-cell receptor and unique sequences; representation of mutation frequency, correlative measures of VJ V, D, J, C, VJ, VDJ, VJC, VDJC, antibody heavy chain, antibody light chain, CDR3, or T-cell receptor usage, etc. Such results may then be output or stored, e.g. in a database of repertoire analyses, and may be used in comparisons with test results, reference results, and the like.

After obtaining an immune repertoire analysis result from the sample being assayed, the repertoire can be compared with a reference or control repertoire to make a diagnosis, prognosis, analysis of drug effectiveness, or other desired analysis. A reference or control repertoire may be obtained by the methods of the invention, and will be selected to be relevant for the sample of interest. A test repertoire result can be compared to a single reference/control repertoire result to obtain information regarding the immune capability and/or history of the individual from which the sample was obtained. Alternately, the obtained repertoire result can be compared to two or more different reference/control repertoire results to obtain more in-depth information regarding the characteristics of the test sample. For example, the obtained repertoire result may be compared to a positive and negative reference repertoire result to obtain confirmed information regarding whether the phenotype of interest. In another example, two "test" repertoires can also be compared with each other. In some cases, a test repertoire is compared to a reference sample and the result is then compared with a result derived from a comparison between a second test repertoire and the same reference sample.

Determination or analysis of the difference values, i.e., the difference between two repertoires can be performed using any conventional methodology, where a variety of methodologies are known to those of skill in the array art, e.g., by comparing digital images of the repertoire output, by comparing databases of usage data, etc.

A statistical analysis step can then be performed to obtain the weighted contribution of the sequence prevalence, e.g. V, D, J, C, VJ, VDJ, VJC, VDJC, antibody heavy chain, antibody light chain, CDR3, or T-cell receptor usage, mutation analysis, etc. For example, nearest shrunken centroids analysis may be applied as described in Tibshirani at al. (2002) P.N.A.S. 99:6567-6572 to compute the centroid for each class, then compute the average squared distance between a given repertoire and each centroid, normalized by the within-class standard deviation.

A statistical analysis may comprise use of a statistical metric (e.g., an entropy metric, an ecology metric, a variation of abundance metric, a species richness metric, or a species heterogeneity metric.) in order to characterize diversity of a set of immunological receptors. Methods used to characterize ecological species diversity can also be used in the present invention. See, e.g., Peet, *Annu Rev. Ecol. Syst.* 5:285 (1974). A statistical metric may also be used to characterize variation of abundance or heterogeneity. An example of an approach to characterize heterogeneity is based on information theory, specifically the Shannon-Weaver entropy, which summarizes the frequency distribution in a single number. See, e.g., Peet, *Annu Rev. Ecol. Syst.* 5:285 (1974).

The classification can be probabilistically defined, where the cut-off may be empirically derived. In one embodiment of the invention, a probability of about 0.4 can be used to distinguish between individuals exposed and not-exposed to an antigen of interest, more usually a probability of about 0.5, and can utilize a probability of about 0.6 or higher. A "high" probability can be at least about 0.75, at least about 0.7, at least about 0.6, or at least about 0.5. A "low" probability may be not more than about 0.25, not more than 0.3, or not more than 0.4. In many embodiments, the above-obtained information is employed to predict whether a host, subject or patient should be treated with a therapy of interest and to optimize the dose therein.

As described herein, a rarefaction analysis of sequence data obtained by any methods described herein may be employed to estimate the completeness of the measurement of immunological repertoire (or of the set of immunological receptors).

Diagnostics and Prognostics

The invention finds use in the prevention, treatment, detection, diagnosis, prognosis, or research into any condition or symptom of any condition, including cancer, inflammatory diseases, autoimmune diseases, allergies and infections of an organism. The organism is preferably a human subject but can also be derived from non-human subjects, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits.

Examples of cancer include prostrate, pancreas, colon, brain, lung, breast, bone, and skin cancers. Examples of inflammatory conditions include irritable bowel syndrome, ulcerative colitis, appendicitis, tonsilitis, dermatitis. Examples of atopic conditions include allergy, asthma, etc. Examples of autoimmune diseases include IDDM, RA, MS, SLE, Crohn's disease, Graves' disease, etc. Autoimmune diseases also include Celiac disease, and dermatitis herpetiformis. For example, determination of an immune response to cancer antigens, autoantigens, pathogenic antigens, vaccine antigens, and the like is of interest.

In some cases, nucleic acids (e.g., genomic DNA, mRNA, etc.) are obtained from an organism after the organism has been challenged with an antigen (e.g., vaccinated). In other cases, the nucleic acids are obtained from an organism before the organism has been challenged with an antigen (e.g., vaccinated). Comparing the diversity of the immunological receptors present before and after challenge, may assist the analysis of the organism's response to the challenge.

Methods are also provided for optimizing therapy, by analyzing the immune repertoire in a sample, and based on that information, selecting the appropriate therapy, dose, treatment modality, etc. that is optimal for stimulating or suppressing a targeted immune response, while minimizing undesirable toxicity. The treatment is optimized by selection for a treatment that minimizes undesirable toxicity, while providing for effective activity. For example, a patient may be assessed for the immune repertoire relevant to an autoimmune disease, and a systemic or targeted immunosuppressive regimen may be selected based on that information.

A signature repertoire for a condition can refer to an immune repertoire result that indicates the presence of a condition of interest. For example a history of cancer (or a specific type of allergy) may be reflected in the presence of immune receptor sequences that bind to one or more cancer antigens. The presence of autoimmune disease may be reflected in the presence of immune receptor sequences that bind to autoantigens. A signature can be obtained from all or a part of a dataset, usually a signature will comprise repertoire information from at least about 100 different immune receptor sequences, at least about $10^2$ different immune receptor sequences, at least about $10^3$ different immune receptor sequences, at least about $10^4$ different immune receptor sequences, at least about $10^5$ different immune receptor sequences, or more. Where a subset of the dataset is used, the subset may comprise, for example, alpha TCR, beta TCR, MHC, IgH, IgL, or combinations thereof.

The classification methods described herein are of interest as a means of detecting the earliest changes along a disease pathway (e.g., a carcinogenesis pathway, inflammatory pathway, etc.), and/or to monitor the efficacy of various therapies and preventive interventions.

The methods disclosed herein can also be utilized to analyze the effects of agents on cells of the immune system. For example, analysis of changes in immune repertoire following exposure to one or more test compounds can performed to analyze the effect(s) of the test compounds on an individual. Such analyses can be useful for multiple purposes, for example in the development of immunosuppressive or immune enhancing therapies.

Agents to be analyzed for potential therapeutic value can be any compound, small molecule, protein, lipid, carbohydrate, nucleic acid or other agent appropriate for therapeutic use. Preferably tests are performed in vivo, e.g. using an animal model, to determine effects on the immune repertoire.

Agents of interest for screening include known and unknown compounds that encompass numerous chemical classes, primarily organic molecules, which may include organometallic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents can comprise cyclical carbon or heterocyclic structures and/or aromatic or polyaromatic structures substituted with one or more of the above functional groups. Candidate agents can also be found among biomolecules, including peptides, polynucleotides, saccharides, fatty adds, steroids, purines, pyrimidines, derivatives, structural analogs or combinations thereof. In some instances, test compounds may have known functions (e.g., relief of oxidative stress), but may act through an unknown mechanism or act on an unknown target.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and can further comprise samples of unknown content. Of interest are complex mixtures of naturally occurring compounds derived from natural sources such as plants, fungi, bacteria, protists or animals. While many samples will comprise compounds in solution, solid samples that can be dissolved in a suitable solvent may also be assayed. Samples of interest include environmental samples, e.g., ground water, sea water, mining waste, etc., biological samples, e.g. lysates prepared from crops, tissue samples, etc.; manufacturing samples, e.g. time course during preparation of pharmaceuticals; as well as libraries of compounds prepared for analysis; and the like (e.g., compounds being assessed for potential therapeutic value, i.e., drug candidates).

Samples or compounds can also include additional components, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, for example from about 0.1 ml to 1 ml of a biological sample can be sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Some agent formulations do not include additional components, such as preservatives, that may have a significant effect on the overall formulation. Thus, such formulations consist essentially of a biologically active compound and a physiologically acceptable carrier, e.g. water, ethanol, DMSO, etc. However, if a compound is liquid without a solvent, the formulation may consist essentially of the compound itself.

Databases of Expression Repertoires and Data Analysis

Also provided are databases of immune repertoires or of sets of immunological receptors. Such databases can typically comprise repertoires results derived from various individual conditions, such as individuals having exposure to a vaccine, to a cancer, having an autoimmune disease of interest, infection with a pathogen, and the like. Such databases can also include sequences of immunological receptors derived from synthetic libraries, or from other artificial methods. The repertoire results and databases thereof may be provided in a variety of media to facilitate their use. "Media" refers to a manufacture that contains the expression repertoire information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression repertoire.

A scaled approach may also be taken to the data analysis. For example, Pearson correlation of the repertoire results can provide a quantitative score reflecting the signature for each sample. The higher the correlation value, the more the sample resembles a reference repertoire. A negative correlation value indicates the opposite behavior. The threshold for the classification can be moved up or down from zero depending on the clinical goal.

To provide significance ordering, the false discovery rate (FOR) may be determined. First, a set of null distributions of dissimilarity values is generated. In one embodiment, the values of observed repertoires are permuted to create a sequence of distributions of correlation coefficients obtained out of chance, thereby creating an appropriate set of null distributions of correlation coefficients (see Tusher at al. (2001) PNAS 98, 5118-21, herein incorporated by reference). The set of null distribution is obtained by: permuting the values of each repertoire for all available repertoires; calculating the pairwise correlation coefficients for all repertoire results; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental repertoires.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among repertoires. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

The analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as drug discovery, analysis of interactions between cellular components, and the like. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output tests datasets possessing varying degrees of similarity to a trusted repertoire. Such presentation provides a skilled artisan with a ranking of similarities and identifies the degree of similarity contained in the test repertoire.

Storing and Transmission of Data

Further provided herein is a method of storing and/or transmitting, via computer, sequence, and other, data collected by the methods disclosed herein. Any computer or computer accessory including, but not limited to software and storage devices, can be utilized to practice the present invention. Sequence or other data (e.g., immune repertoire analysis results), can be input into a computer by a user either directly or indirectly. Additionally, any of the devices which can be used to sequence DNA or analyze DNA or analyze immune repertoire data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground man, air mail). Thus, data collected by the methods described herein can be collected at any point or geographical location and sent to any other geographical location.

Reagents and Kits

Also provided are reagents and kits thereof for practicing one or more of the above-described methods. The subject reagents and kits thereof may vary greatly. Reagents of interest include reagents specifically designed for use in production of the above described immune repertoire analysis. For example, reagents can include primer sets for cDNA synthesis, for PCR amplification and/or for high throughput sequencing of a class or subtype of immunological receptors. Gene specific primers and methods for using the same are described in U.S. Pat. No. 5,994,076, the disclosure of which is herein incorporated by reference. Of particular interest are collections of gene specific primers that have at least 2, 5, 10, 15, 20, 30, 40, 50, 60, 70, 80, 90, 100, 200, 300, 400, 500, 600, 700, 800, 900, 1000 primer sets or more. The gene specific primer collections can include only primers for immunological receptors, or they may include primers for additional genes, e.g., housekeeping genes, controls, etc.

The kits of the subject invention can include the above described gene specific primer collections. The kits can further include a software package for statistical analysis, and may include a reference database for calculating the probability of a match between two repertoires. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed, site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

Software products (or components) may be tangibly embodied in a machine-readable medium, and comprise instructions operable to cause one or more data processing apparatus to perform operations comprising: a) clustering sequence data from a plurality of immunological receptors or fragments thereof; and b) providing a statistical analysis output on said sequence data. Also provided herein are software products (or components) tangibly embodied in a machine-readable medium, and that comprise instructions operable to cause one or more data processing apparatus to perform operations comprising: storing sequence data for more than $10^2$, $10^3$, $10^4$, $10^5$, $10^6$, $10^7$, $10^8$, $10^9$, $10^{10}$, $10^{11}$, or $10^{12}$ immunological receptors or more than $10^2$, $10^3$, $10^4$, $10^5$, $10^6$, $10^7$, $10^8$, $10^9$, $10^{10}$, $10^{11}$, or $10^{12}$ sequence reads.

In some examples, a software product (or component) includes instructions for assigning the sequence data into V, D, J, C, VJ, VDJ, VJC, VDJC, or VJ/VDJ lineage usage classes or instructions for displaying an analysis output in a multi-dimensional plot. In some cases, a multidimensional plot enumerates all possible values for one of the following: V, D, J, or C. (e.g., a three-dimensional plot that includes one axis that enumerates all possible V values, a second axis that enumerates all possible values, and a third axis that enumerates all possible J values). In some cases, a software product (or component) includes instructions for identifying one or more unique patterns from a single sample correlated to a condition. The software product (or component0 may also include instructions for normalizing for amplification bias. In some examples, the software product (or component) may include instructions for using control data to normalize for sequencing errors or for using a clustering process to reduce sequencing errors. A software product (or component) may also include instructions for using two separate primer sets or a PCR filter to reduce sequencing errors.

EXAMPLES

The following examples are offered by way of illustration and not by way of limitation.

Lineage Structure of the Human Antibody Repertoire in Response to Influenza Vaccination The human antibody repertoire is one of the most important defenses against infectious disease, and the development of vaccines has enabled the conferral of targeted protection to specific pathogens. However, there are many challenges to measuring and analyzing the immunoglobulin sequence repertoire, such as the fact that each B cell contains a distinct antibody sequence encoded in its genome, that the antibody repertoire is not constant but changes over time, and the high similarity between antibody sequences. We have addressed this challenge by using high-throughput long read sequencing to perform immunogenomic characterization of expressed human antibody repertoires in the context of influenza vaccination. Informatic analysis of 5 million antibody heavy chain sequences from healthy individuals allowed us to perform global characterizations of isotype distributions, determine the lineage structure of the repertoire and measure age and antigen related mutational activity. Our analysis of the clonal structure and mutational distribution of individuals' repertoires shows that elderly subjects have a decreased number of lineages but an increased pre-vaccination mutation load in their repertoire and that some of these subjects have an oligoclonal character to their repertoire in which the diversity of the lineages is greatly reduced relative to younger subjects. We have thus shown that global analysis of the immune system's clonal structure provides direct insight into the effects of vaccination and provides a detailed molecular portrait of age-related effects.

The adaptive immune system produces a large and diverse set of antibodies, each with an individual evolutionary and clonal history. This so called "antibody repertoire" protects each individual against insults such as infection and cancer, and responds to vaccination with B cell proliferation in response to the antigenic stimulation. Hybridomas and antigen-specific FACS-based analysis have given us much insight on how the immune system generates the complex and diverse immune response required to protect the body from the wide variety of potential pathogens. However, these methods have not been sufficient to make global and unbiased characterizations of the clonal structure of the immune system of a particular individual, which could provide insights into how the diversity and clonal structures vary between individuals, with age or gender, and in response to specific antigen stimulation. With respect to antigen stimulation, although there is a great deal of data that has been obtained by sorting antigen specific B cells, there is less information on the effect of the antigen on the global response of the antibody repertoire.

We have applied high-throughput sequencing techniques to the immunogenetic characterization of antibody repertoire. The repertoire of individuals has a surprising high fraction of shared sequences, a universal structure and that the balance between determinism and stochasticity in the repertoire is tilted more towards determinism both in early development and in the primary repertoire of mature organisms than had previously been suggested. Attempts to use this approach to study vaccination have not been able to resolve lineage relationships and have not demonstrated a functional link between repertoire and immune response. Here, we address the question of how the human immune repertoire responds to specific antigen stimulation, in particular by influenza vaccination. We determine the lineage structure of the repertoire before and after vaccination and demonstrate that some sequences in the repertoire correspond to vaccine-specific immunoglobulins. We further observe age related changes in antibody isotype composition, lineage diversity and structure, as well as mutational bad, thereby offering a molecular characterization of defects in humoral immune response resulting from aging.

Results

We analyzed antibody repertoires from peripheral blood drawn from 17 human volunteers who were immunized with 2009 or 2010 seasonal influenza vaccines (Table 1). These volunteers were recruited from three age groups, children (8 to 17 years of age), young adults (18 to 30 years of age), and elderly (70 to 100 years of age) and were randomly given either trivalent inactivated influenza vaccine (TIV) or live attenuated influenza vaccine (LAIV), except for subjects in the 70 to 100 years group who could only receive TIV (Table 1). TIV and LAIV contain antigenically equivalent virus strains, however LAIV is made of live attenuated viruses that are capable of limited proliferation after intranasal administration and are expected to induce a stronger mucosal immune response than TIV. The study included three pairs of identical twins in order to have repertoire control experiments with identical genetic background; these were in the age group of 8 to 17 and were randomly selected to receive either TIV or LAIV within a twin pair. Blood samples were collected from each participant at three time points: day 0 before vaccination (visit 1), day 7 or 8 (visit 2), and day 28 (±4, visit 3) after vaccination. Peripheral blood mononuclear cells (PBMCs) were collected at both visit 1 and 3. Naïve B cells (NB) and plasmablasts (PB) were sorted from visit 2 blood samples by flow cytometry.

Figure 7:
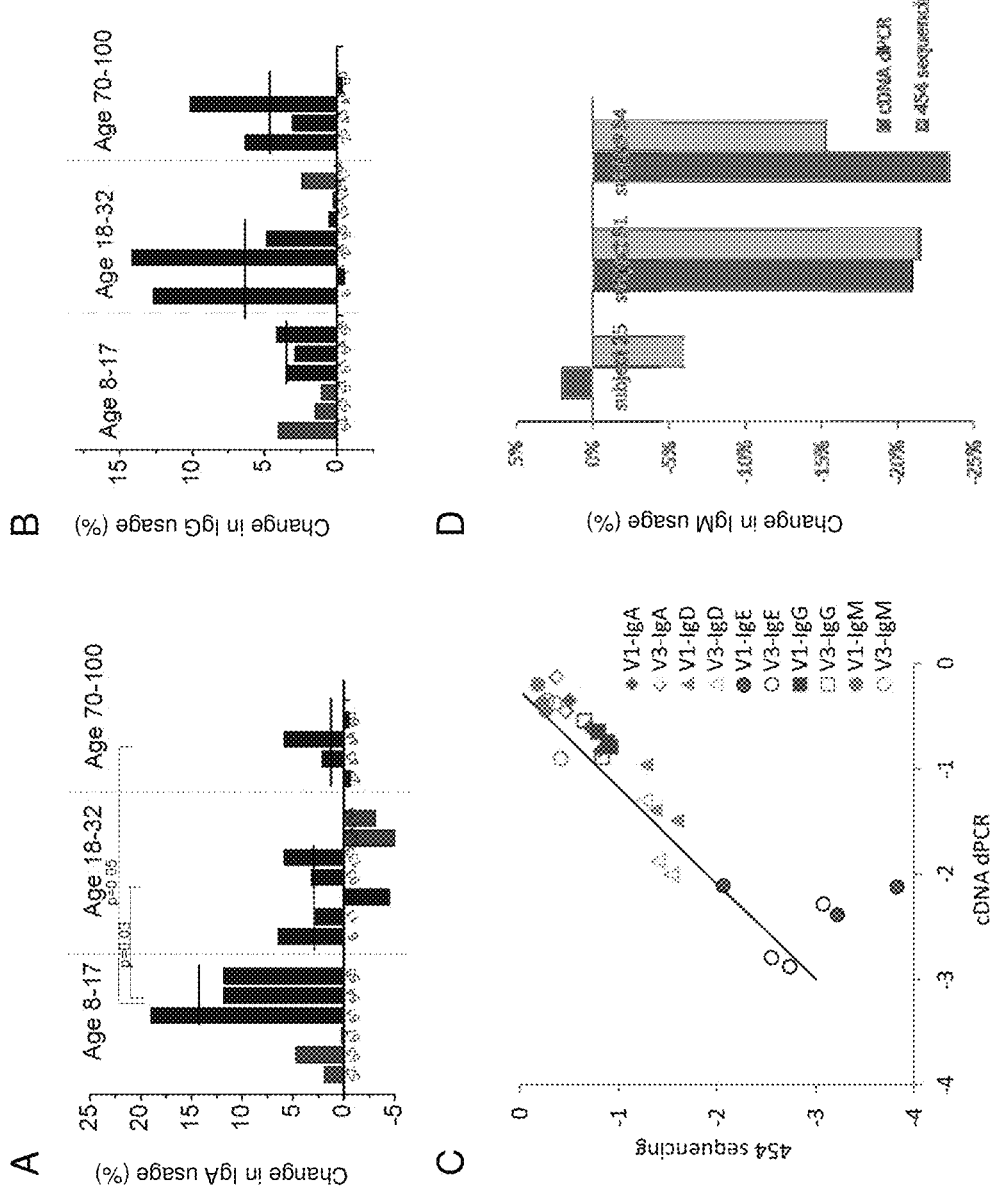
FIG. 7. Isotype changes from visit 1 to visit 3. (A), changes in individual's IgA usage in PBMCs from visit 1 to visit 3. IgA usage increases 14.21% (age 8-17), 2.77% (age 18-32) and 1.71% (age 70-100) at visit 3 on average for TIV receivers (black lines). (B), increase in individual's IgG usage in PBMCs from visit 1 to visit 3. IgG usage increases 3.4% (age 8-17), 6.3% (age 18-32) and 4.8% (age 70-100) at visit 3 on average for TIV receivers (black lines). The subject IDs are labeled on horizontal axis. 3000 reads of subsampling was not applied here, all reads were taken into calculation. Red, LAIV receivers; blue, TIV receivers. Children who received TIV were more likely to have an increased relative IgA usage compared to young adults (p=0.03, Mann-Whitney U test) or elderly (p=0.05, Mann-Whitney U test). Isotype composition was also verified by dPCR (23, 24) for three selected subjects. (C), Correlations of 5 antibody isotype compositions (percentage in log scale) between two different measurements (dPCR and 454 sequencing) for three subjects using PBMCs from visits 1 and 3. (D), Changes of relative IgM composition between visits 1 and 3 for these three subjects.
Figure 8:
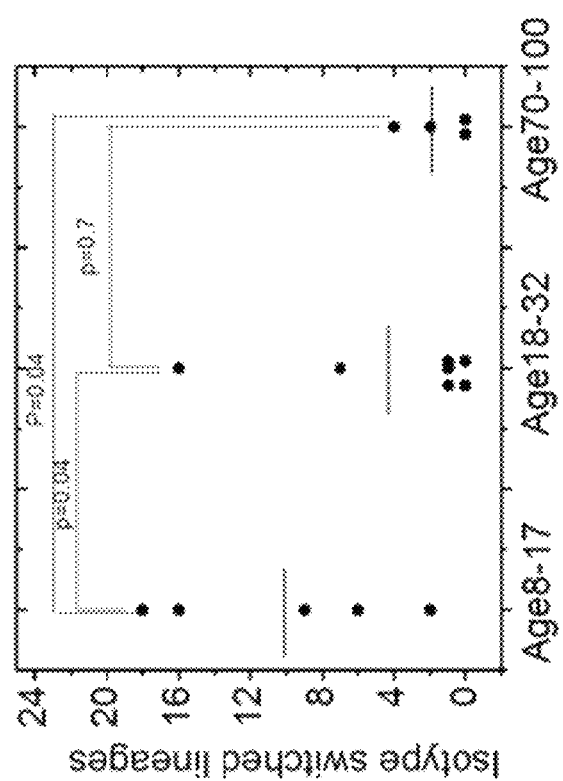
FIG. 8. Young subjects have more lineages that are isotype switched. For each subject, we pooled all IgM and IgG sequences and performed single linkage clustering as defined before. If a lineage is composed of both IgM and IgG sequences, this lineage is defined as an isotype switched lineage. p-values were calculated using Mann-Whitney U test.
Figure 9:
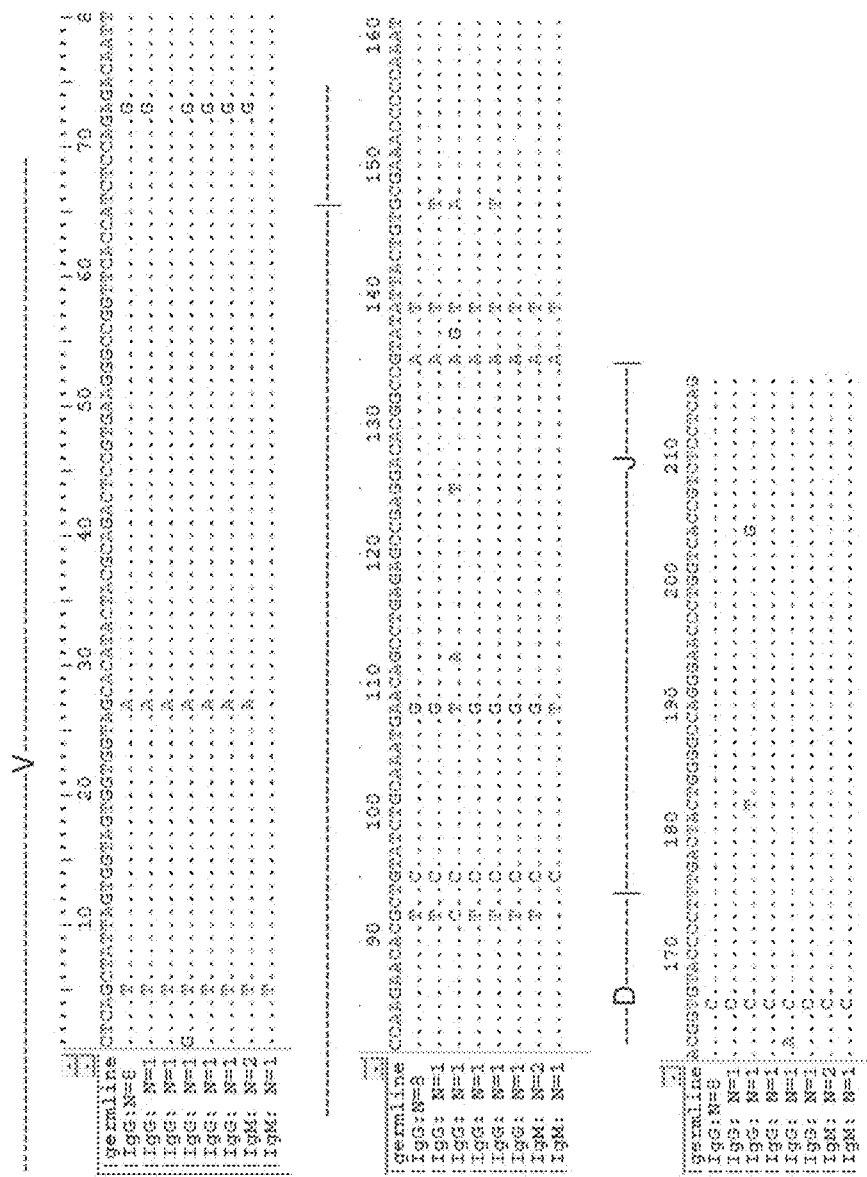
FIG. 9. Nucleotide sequence alignment for VDJ region exemplified for one isotype switched lineage. Sequence titles indicate isotype and numbers after N denote number of reads. ("germline" sequence - SEQ ID NO: 22)

Reduction of relative 104 abundance after vaccination decreases with age. All five isotypes were detected in all the samples processed, however, with different relative amounts. IgM, IgA and IgG are more abundant than IgD and IgE, which together account for less than 4% of all sequencing reads (FIG. 1A). Most naïve B cells express IgM on their membrane, and then upon antigen stimulation undergo an activation process that changes their constant region from IgM to other isotypes and increases the antibody transcript copy numbers in each cell. We tracked the changes of isotype distribution between visit 1 and visit 3 and noticed a decrease of relative IgM abundance for all volunteers except one (FIG. 1B). On average, relative IgM usage decreased 11.1%±3.2 (SEM) (age 8-17), 6.5%±2.4 (SEM) (age 18-32) and 6.0%±2.9 (SEM) (age 70-100) at visit 3 (FIG. 1B, black lines). An independent measurement by digital PCR was used to verify the relative isotype abundance in visit 1 and 3 samples and the reduction of relative IgM abundance from visit 1 to visit 3 (FIG. 7). This decrease coincided with an increase of relative IgA and IgG abundance (FIG. 7), suggesting that a portion of the naïve B cells may have undergone isotype switching and the antibody transcript copy numbers of these isotypes may also have increased as a result of the vaccine stimulation. This interpretation is supported by flow cytometry data which did not show changes in the relative abundances of IgM expressing cells between visits 1 and 3. Therefore, the large difference in relative IgM usage is due to antibody transcript copy number changes as a result of antigen stimulation. We also directly observed isotype switched lineages in a small fraction of the sequence data. These sequences contained common CDR3 sequences and had extensive mutations throughout the variable regions (FIG. 9), which suggests that they are not template-switched PCR artifacts. The number of lineages containing isotype-switches decreased with age, (FIG. 8) which is consistent with our observation that reduction of relative IgM transcript abundance from visit 1 to visit 3 decreases with age regardless of vaccine types (FIG. 1C). While LAIV receivers have less change in relative IgM usage than individuals who received TIV, there is a strong age dependence of isotype relative abundance change in TIV receivers—children who received TIV were more likely to have an increased relative IgA usage compared to young adults (p=0.03, Mann-Whitney U test) or elderly (p=0.05, Mann-Whitney U test) (FIG. 7).

Single linkage clustering enables informatic definition of lineages. One crucial aspect of clonal expansion after antigen stimulation is that activated B cells undergo a somatic hypermutation process during which random mutations are introduced to the antibody genes. Clonal expansion is therefore not truly clonal as a key aspect is also the introduction of new diversity, followed by selection for the mutants with higher antibody affinity. Distinguishing mutations, grouping sequences that differ by somatic hypermutation to the same clonal lineage, and following the sequence evolution within a lineage are critical steps in understanding B cell biology and the relationship between B cell repertoire and vaccine stimulation. High throughput sequencing enables one to directly measure these relationships at a scale that was not possible with earlier approaches.

Figure 5:
FIG. 5. Flowchart of bioinformatics pipeline. Whether the translated protein was in frame or not was determined by the constant region. The amino adds at the beginning of constant region of correct frame are S-P (IgA), P-T (IgD), S (IgG), S-A-S (IgM). For many samples, IgE accounts for less than 1% of the reads and therefore was not considered further in the analysis.
Figure 10:
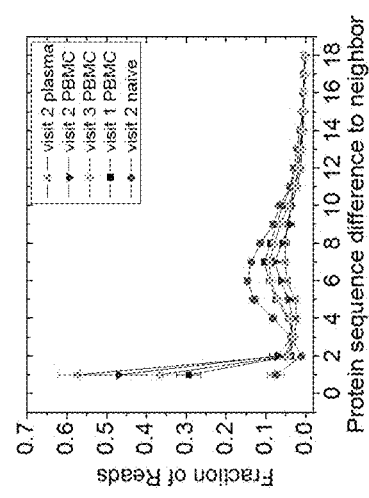
FIG. 10. Reads distribution based on relative sequence distance. For each reads in a sample, we search in the entire repertoire of this sample to find the neighboring read with minimum difference in the CDR3 region at protein sequence level. Distribution of reads with minimum distance to its neighbor were plotted. Sub-sampling of 3000 reads was performed.
Figure 11A:
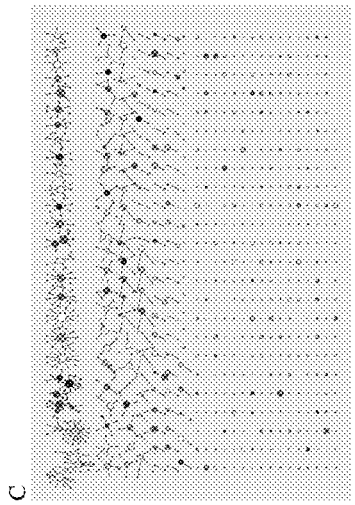
FIG. 11. The inter- and intra-lineage structure of all IgG lineages revealed by sequencing plasmablasts sorted from the visit 2 blood samples for selected subjects. Subject 53 (panel A, 9762 reads), subject 29 (panel B, 28712 reads) and subject 25 (panel C, 27079 reads),In this network representation, each cluster of dots connected by lines stands for a lineage. Different colors were used to distinguish different lineages. Each dot represents a unique CDR3 protein sequence. Two dots are linked if they differ by one amino acid in the CDR3 region as defined by the clustering threshold. The area of a dot is proportional to the number of reads with identical CDR3 protein sequences. Plots were generated using Pajek. (D), graphical presentation of an intra-lineage structure for the top lineage in panel. Arrows indicate direction of mutation increase. (E), AA sequences alignment of the CDR3 (B:183/11 - SEQ ID NO: 23). Lines separate sequences belong to each node as indicated by letter A, B, C and D in panel D. In the headers of the alignment, X/Y means that the sequence has X identical reads in AA, and the average mutation to germline is Y in nucleotide.
Figure 11A:
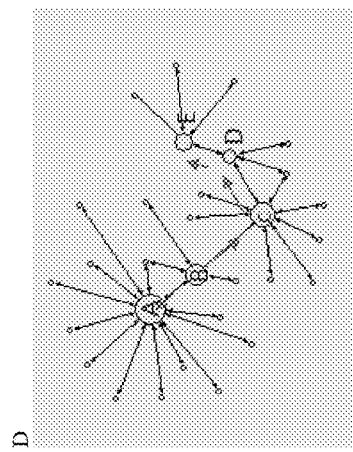
Figure 11A:
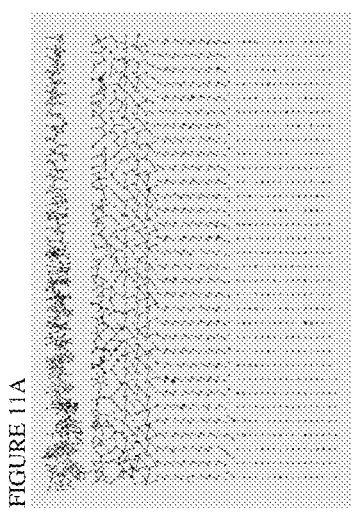
Figure 11A:
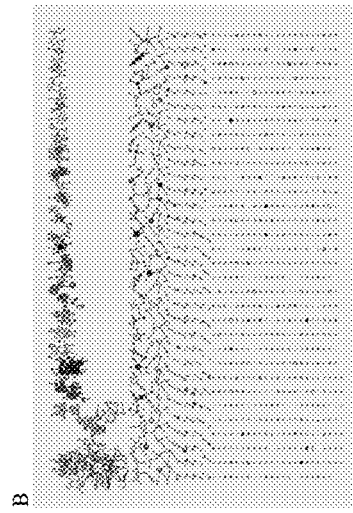
Figure 11A:
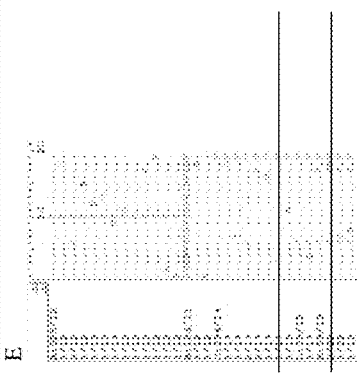

To dissect differences between lineages and analyze the detailed mutations within a lineage, we developed a clustering scheme that focused on the complementarity determining region 3 (CDR3) of the antibody sequence, which covers the region between the end of V and beginning of J gene segments. We first converted the nucleotide sequences into amino acid sequences for each read. Translation rescue was performed for out-of-frame sequences that were mostly due to insertions and/or deletions in the V, D, or J segments (FIG. 5). In order to set the clustering threshold, we analyzed the amino acid distance between reads in the CDR3 region. The resulting distribution showed two distinct peaks; the first is at 1 amino acid and the other covers 4 to 10 amino acids (FIG. 10). This suggests that the first peak contained sequencing reads that were mostly mutated and the second peak contained sequencing reads that had distinct CDR3 sequences that were generated during the VDJ recombination process. The amplitude of these two peaks changed between different samples that were collected at different time points and had varying NB and PB cell fractions. Sorted NBs had the lowest first peak and highest second peak, while sorted PBs has the highest first peak and the lowest second peak. PBMC samples from visit 1 and 3 fell in between NBs and PBs while visit 2 PBMCs (available only for selected subjects) were similar to visit 2 PBs. These trends are consistent with dynamics of antibody mediated immune response and distribution of NBs and PBs in peripheral blood. These trends further demonstrated that the first peak is due to mutation and second peak is due to junctional diversity.

Figure 2:
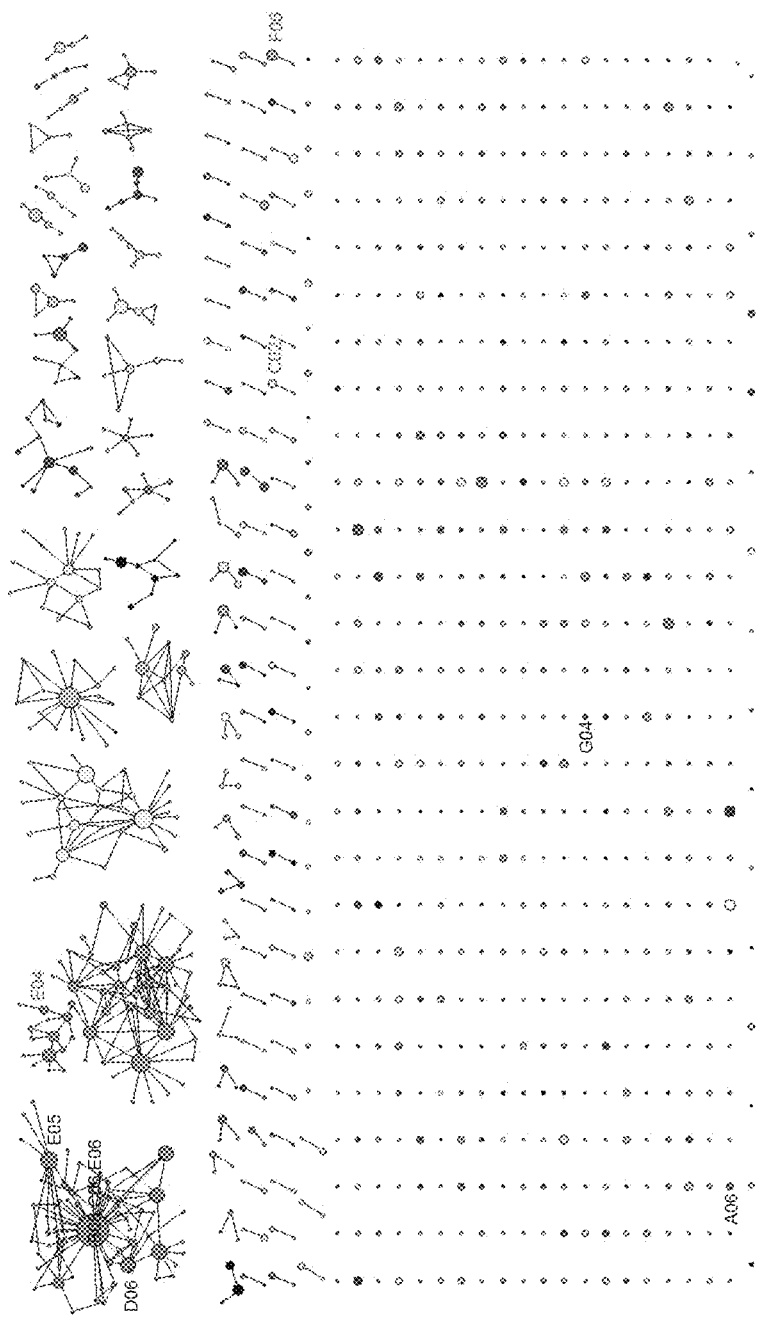
FIG. 2. Informatically defined lineages with influenza specificity. The intra- and inter-lineage structure of all IgG lineages visualized by sequencing the PBs sorted from blood sample collected at visit 2 (7 days after vaccination) from a volunteer in the 70-100 year-old group received TIV (subject 017-043). In this network representation, each cluster of dots connected by lines represents a lineage. Different colors were used to distinguish different lineages. Each dot represents a unique CDR3 protein sequence. Two dots are linked if they differ by one amino add in the CDR3 region. This is the threshold used when performing the single linkage clustering. The area of a dot is proportional to the number of reads with identical CDR3 protein sequences. Single cell cloned antibodies are labeled with text. Red text indicates antibodies having a high affinity towards one of the virus strains used in the flu vaccine. Black text indicates antibodies with a low affinity towards one of the virus strains used in the flu vaccine or background level of binding towards all three virus strains. 8 of 10 single cell cloned antibodies were found in the 454 sequences, except G04 and A06. All reads from 454 sequencing were used for this plot.
Figure 19:
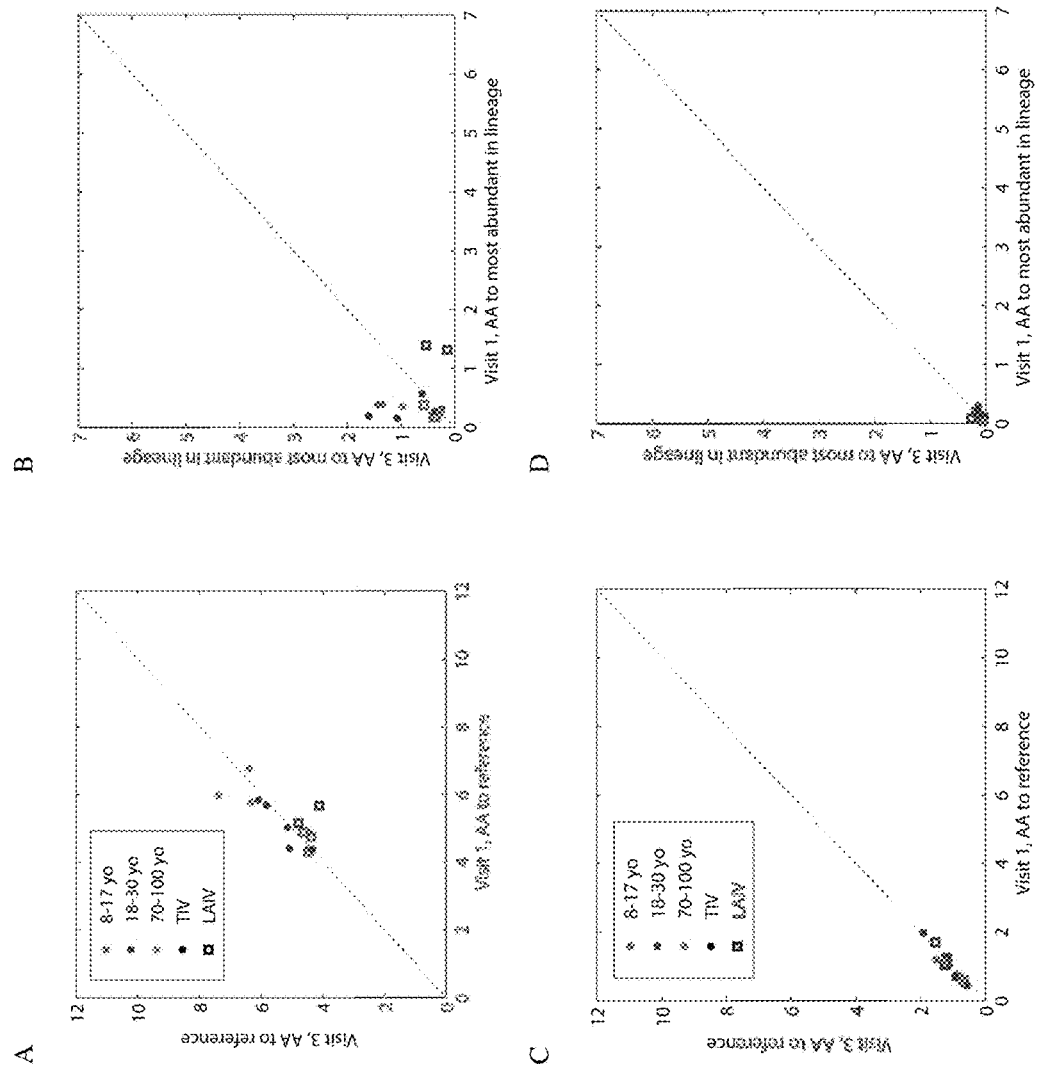
FIG. 19. The mutation patterns for different age groups at threshold of 90% of nucleotide similarity in the CDR3 region. This analysis was applied to IgG in the PBMCs at visit 1 (A, B) and IgM in the PBMCs at visit 1 (C, D). 3000 reads of subsampling was applied to this figure.

This distribution provides a natural threshold when clustering and was used to group sequences according to their lineage identity. We also performed clustering directly on nucleotide sequences with varying thresholds (FIG. 19). Here "lineage" refers to antibody sequences that originated from the same VDJ recombination event and have the same junctional sequence, but may be further diversified because of antigen stimulation and somatic hypermutation. We clustered all sequencing reads from sorted PBs at visit 2 using one amino acid difference at CDR3 as a threshold. This means that two sequences will be grouped into the same lineage if they are in the same V and J family and their protein sequence in the CDR3 region differ by no more than one amino acid. Using this lineage data, one can construct a graphical representation of the clonal structure of the immune repertoire (FIG. 2 and FIG. 11). The central functional question regarding these informatically defined sequence lineages is to what extent they include influenza specific antibodies.

Figure 15:
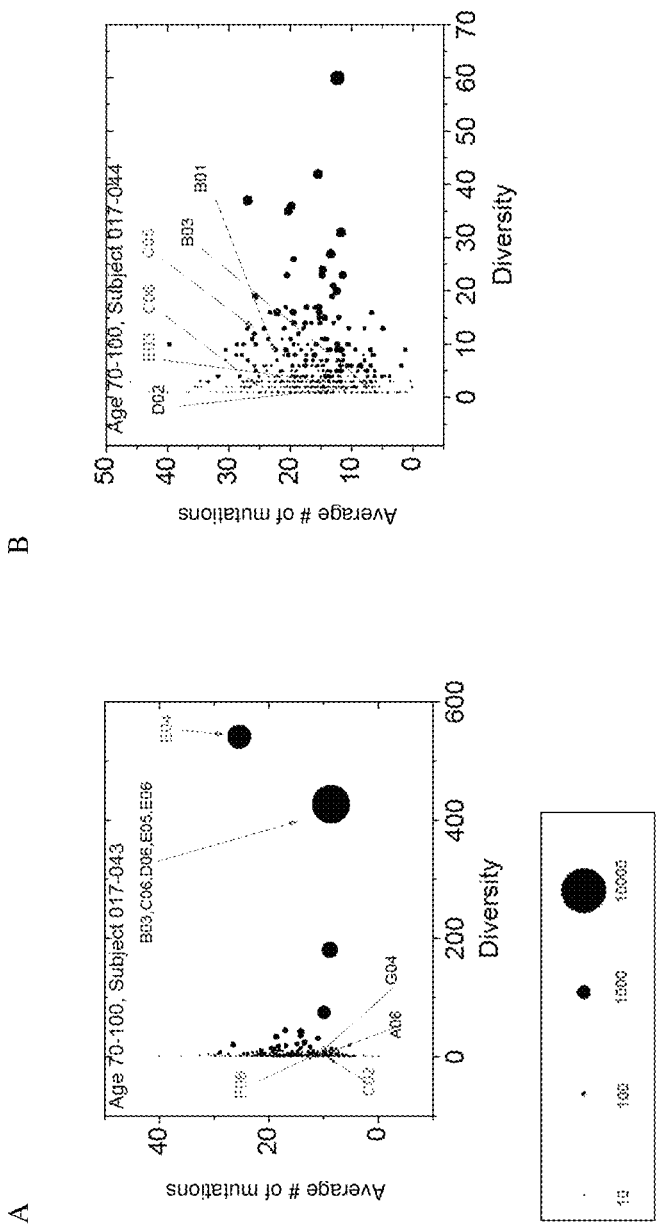
FIG. 15A-B. Overlapping of single-cell cloned antibody sequences with lineages. Single cell cloning and high-throughput sequencing were performed on the same pool of sorted plasmablasts from two volunteers. Sequence overlapping between the two methods was demonstrated. The plot was generated the same way as Supplementary FIG. 8. Single cell cloned antibodies are labeled with text. Red text indicates antibodies having a high affinity towards one of the virus strains used in the flu vaccine. Black text indicates antibodies with a low affinity towards one of the virus strains used in the flu vaccine or background level of binding towards all three virus strains. Antibodies G04, A06 in subject 017-043, and B03, C06, and D02 in subject 017-044 were not found in our high-throughput sequencing data. Please note that all reads are included in plotting these two figures, rather than using 3000 reads subsampling. To avoid the overlapping of dots, the size of the dots is scaled down 4 fold from number of sequencing reads, see the scale bar at the bottom.

To examine this, we amplified influenza-specific antibody sequences from single sorted PBs for two of the subjects in the 70-100 years old group, 017-043 and 017-044. We then expressed monoclonal antibodies according to these sequences and verified their binding to each of the three virus strains in the vaccine. 11 out of 16 heavy chain sequences from single cell cloned PBs were found within the lineages we measured, especially for the anti-vaccine high affinity antibodies (FIG. 2). For subjects 017-044, the single cell cloned sequences overlap with lineages containing smaller number of reads compared to sequences cloned from 017-043, where many single cell cloned sequences are in the top lineage containing most of the reads (FIG. 15). This may reflect structural differences in repertoire between these two subjects as one has a dominant lineage and the other one has a more even distribution (FIG. 15). Taken together, these data confirm that the influenza specific antibody responses are contained within the globally measured immune repertoire sequences as well as the informatically defined lineages we derived from them.

Figure 3:
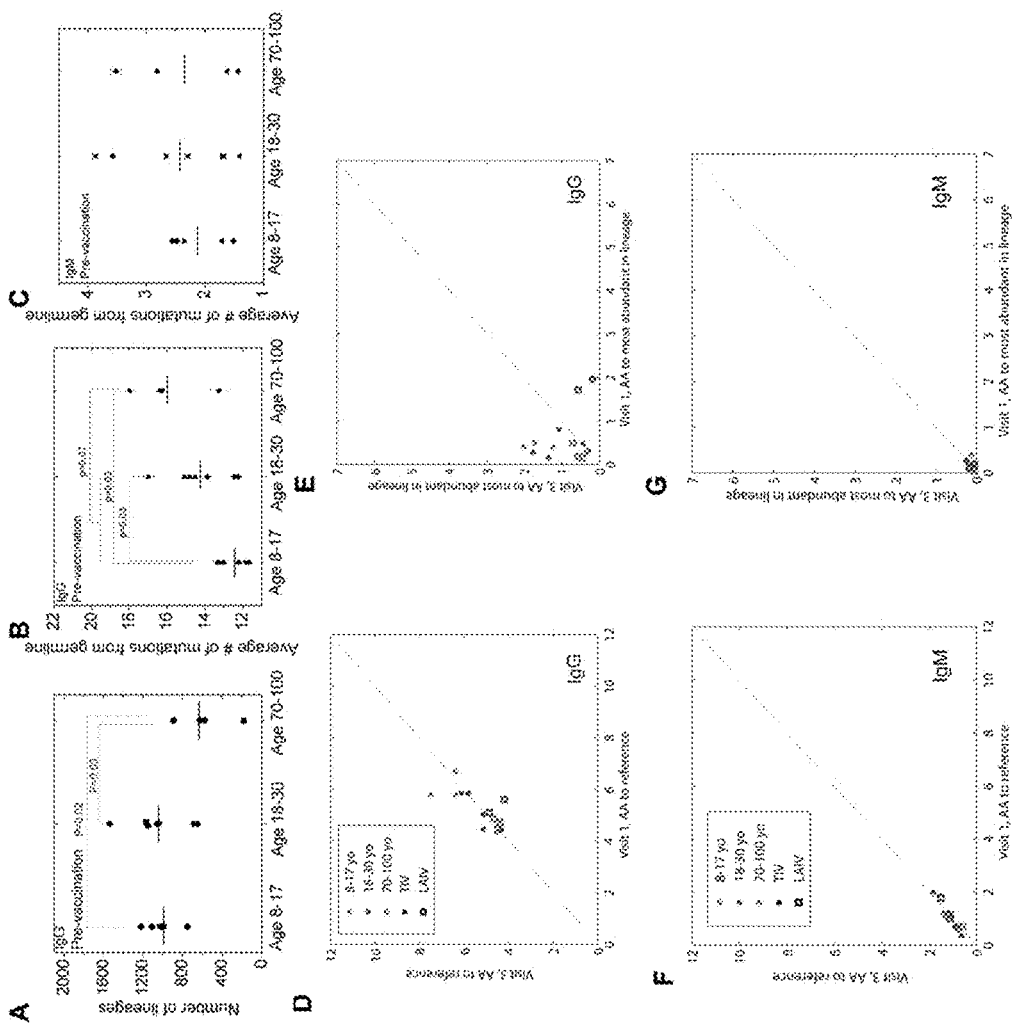
FIG. 3. Age related repertoire diversity and mutation changes. (A), repertoire diversity changes with age as measured by number of lineages in IgG from visit 1 PBMCs. (B and C), before vaccination mutation load as measured by averaging mutations at nucleotide level for IgG (B) and IgM (C) in visit 1 PBMCs respectively. Mutations for each read were defined as the number of mismatches to germline reference in V, D and J regions. (D-G), lineage analysis, performed with 80% nucleotide-sequence identity at the VDJ junctional region, gives measurements of amino add mutations-per-read at V and J gene segments measured ether to the germline reference (D and F) or from the most abundant sequence of the lineage to which each belongs (E and G) for IgG (D and E) and IgM (F and G). X-axes denote the measurement at visit 1, and the Y-axes denote the measurement at visit 3. Elderly patients show a higher number of IgG mutations from the germline (comparing 8-30 year-olds to 70-100 year-olds gives p<0.075 before vaccination and p<0.0044 after; restricting this analysis to TIV-patients alone gives p<0.18 and p<0.017, respectively).
Figure 16:
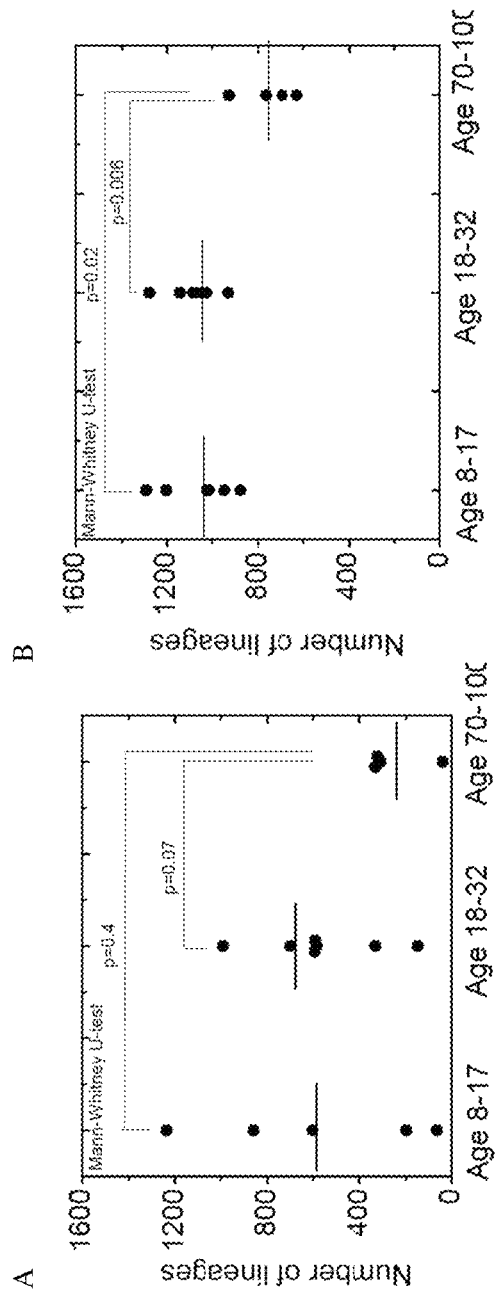
FIG. 16. Repertoire diversity changes with age. Repertoire diversity changes with age as measured by number of lineages in IgG from visit 2 plasmablasts (A) and IgG from visit 3 PBMCs (By p value was calculated by Mann-Whitney U test. 3,000 reads subsampling was applied. There are 6 samples in the age group 8-17, 7 samples in the age group 18-32, 4 samples in the age group 70-100.
Figure 17:
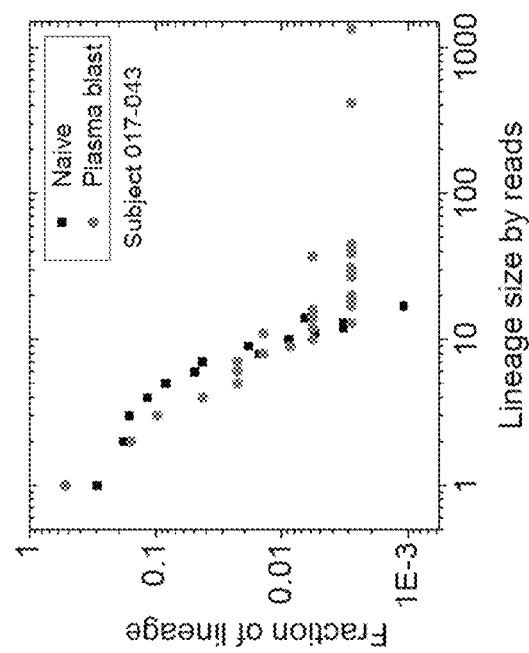
FIG. 17. Distribution of lineage size observes the power-law distribution. IgG lineages defined for the plasmablasts display a power-law distribution with a fat tail. The exponent of the power law is −1.7. The IgM lineage size distribution of naïve B cell does not exhibit this fat tail. 3000 reads of subsampling was applied to this figure.

Lineage structure analysis reveals distortion in some elderly subjects. Lineages belonging to plasmablasts exhibit an apparent power law distribution with a few lineages that dominate the repertoire, whereas those belonging to naïve cells do not (FIG. 17). This is consistent with long-tailed distributions observed previously and are the direct consequence of clonal expansion. The elderly have fewer lineages than other age groups both before (FIG. 3A) and after (FIG. 16) vaccination, indicating an altered repertoire structure and potentially a smaller pool of diversity for the immune repertoire to draw upon in vaccine response.

Figure 4:
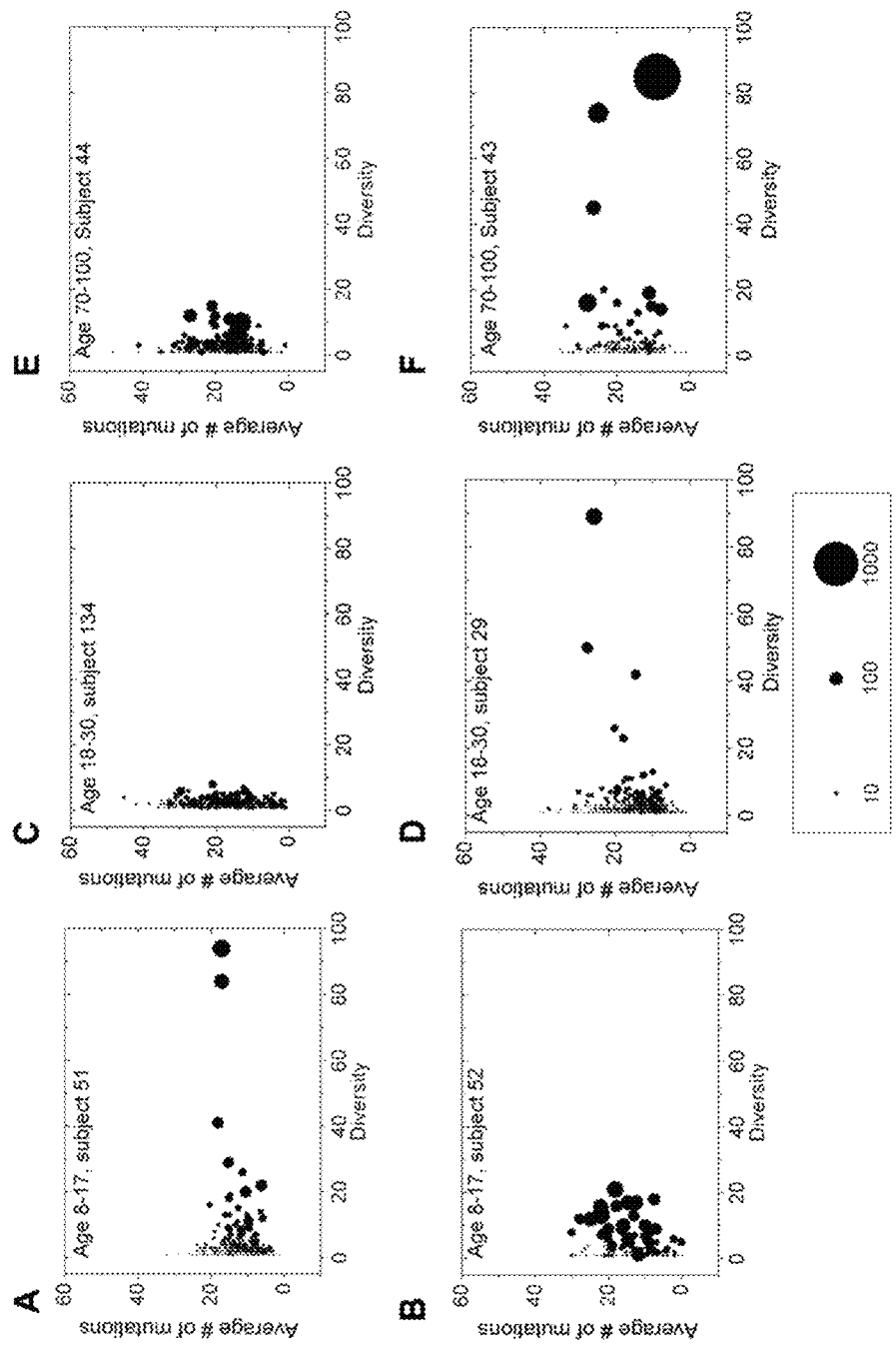
FIG. 4. Inter-lineage structure of IgGs in visit 2 PBMCs. Inter-lineage structure of IgGs in visit 2 PBMCs is presented for six randomly selected subjects (A-B, age 8-17; C-D, age 18-32; E-F, age 70-100). Each dot represents a lineage of antibody sequences defined by single linkage clustering with 1 amino add difference at CDR3 as the threshold. The area of the dot is proportional to the number of reads belonging to this lineage, as indicated in the scale bar. X-axis is the diversity of the lineage which measures number of unique protein sequences (full protein sequence, not just the CDR3 region) within the lineage. Y-axis is the number of mutations at nucleotide level of the lineage averaged over reads. 3000 reads of subsampling was applied.
Figure 12I:
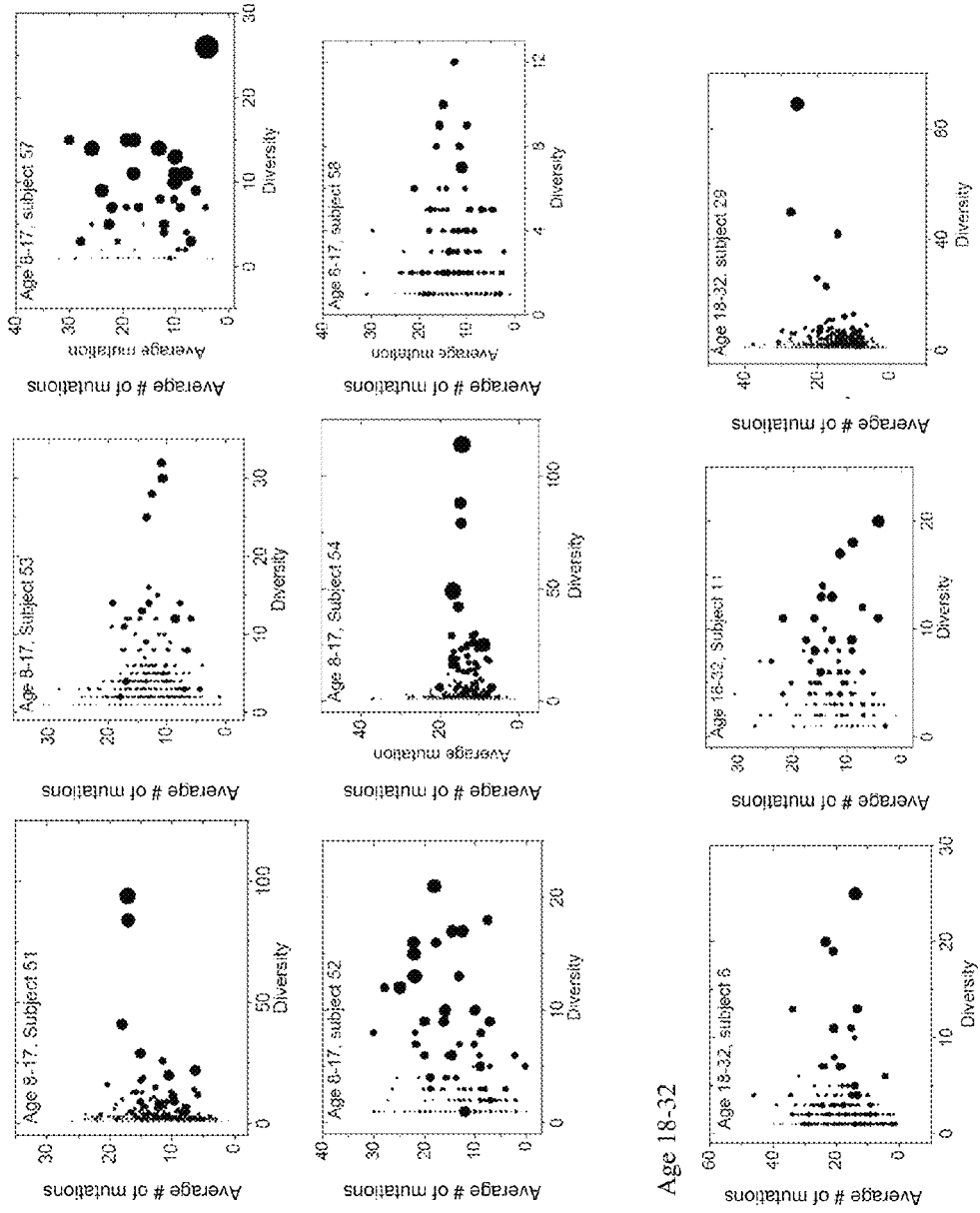
FIGS. 12i and 12ii. The inter-lineage structure of IgG from plasmablasts sorted for all subjects at visit 2. Each panel represents one volunteer. In each panel, each dot represents a lineage of antibody sequences defined by single linkage clustering with 1 amino add difference at CDR3 as the threshold. The area of the dot is proportional to the number of reads belongs to this lineage, as indicated in the scale bar in the last panel. X-axis is the diversity of the lineage which measures number of unique protein sequences (full protein sequence, not just the CDR3 region) within the lineage. Y-axis is the number of mutation at nucleotide level of the lineage averaged over reads. Subject 017-051 and subject 017-052, subject 017-053 and subject 017-054, and subject 017-057 and subject 017-058 are twin pairs. 3000 reads of subsampling was applied to this figure.
Figure 13:
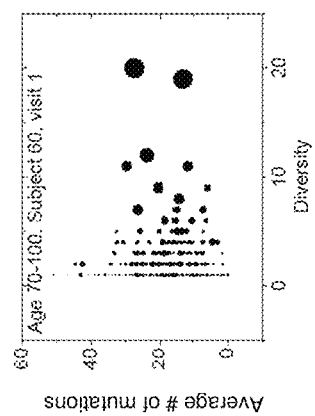
FIG. 13. The inter-lineage structure of IgG from PBMCs purified from subject 017-060 at visit 1. The plot was generated the same way as Supplementary FIG. 5. This is in contrast to the lineage structure of plasmablasts sorted for the same subject at visit 2 (Supplementary FIG. 5). The dominant lineage of subject 017-080 at visit 2 is not observed in visit 1. 3000 reads of subsampling was applied to this figure.
Figure 14:
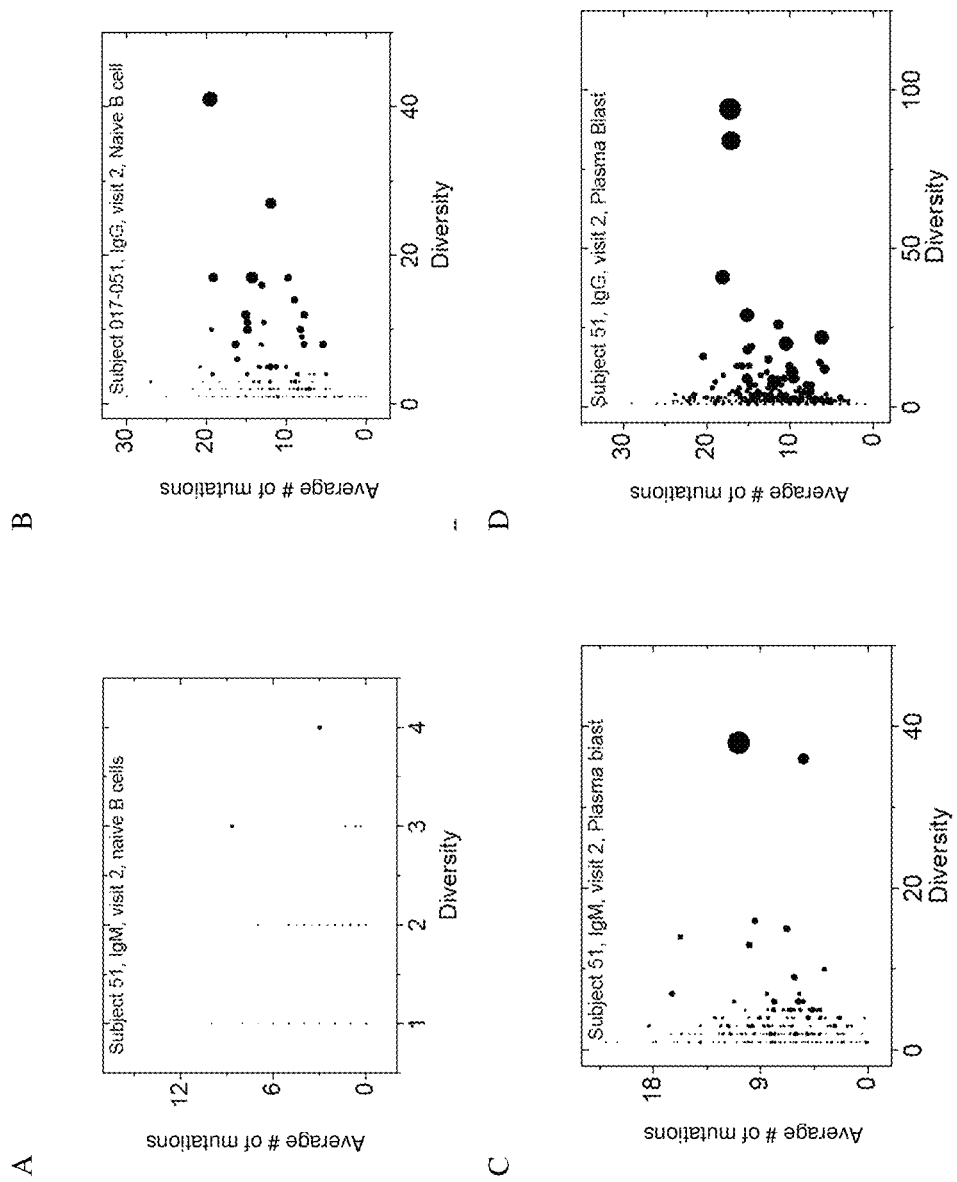
FIG. 14A-D. The inter-lineage structure of IV and IgG for naïve B cells and plasmablasts from one subject at visit 2. The plot was generated the same way as Supplementary FIG. 5. Naïve B cells display minimum intra-lineage diversity (number of unique sequences within a lineage) compared to plasmablasts from the same subject. Most lineages in naïve B cell has only one read with no mutations, especially for the IgM isotype. IgM and IgG account for 60% and 21% of reads in subject 51's naïve B cells. IgM and IgG account for 10% and 63% of reads in subject 51's plasmablasts respectively. The average IgM in naïve B cells of all subjects is 75%. The average IgG in plasmablasts of all subjects is 63%. 3000 reads of subsampling was applied to this figure.

Using the three parameters of diversity (unique protein sequences), average mutation, and number of reads in each lineage, one can visualize and compare the antibody repertoire in a quantitative manner (FIG. 4A-F). In each individual, the majority of the lineages contain less than 10 reads and less than two unique amino acid sequences. The elderly vaccine recipients can be separated into two groups: one group had a distribution of lineages similar to the children (FIGS. 4A and B) and young adults (FIGS. 4C and D); the other group had a very different distribution of lineages compared to other age groups (FIGS. 4E and F). Elderly subjects in the second group had a few lineages that encompassed more than 80% of the reads. This is exemplified by subject 017-43 (FIG. 4F, and FIGS. 12 and 15). Detailed sequence analysis revealed that 58% (subject 017-043) and 90% (subject 017-060) of the reads within the biggest lineage for these elderly were identical. This is consistent with the overall observation that influenza vaccination resulted in expansion of far fewer B cell lineages in the elderly compared to the other age groups (FIG. 16A). This reduced clonal diversity when weighted with abundance may be related to a reduced antibody response to influenza vaccine in the elderly. Lineage analysis on IgG from visit 1 and 3 PBMCs also suggested that in general the elderly have a reduced B cell clonal diversity compared to the younger age groups (FIG. 3A and FIG. 16B), which might explain the reduced clonal diversity in vaccine-activated B cells in the elderly.

Age affects somatic hypermutation and lineage diversity. One interesting question about reduced immune response to influenza vaccination in the elderly is whether the B cells that respond to the current vaccine had been primed by prior infections or vaccinations. If so, those B cells from the elderly will mostly likely be memory B cells that have a higher baseline mutation than responding B cells from younger volunteers where most of these cells should be of naïve phenotype or relatively less antigen experienced, therefore, have fewer mutations. Another important question is whether those responding memory B cells in the elderly have the same ability to introduce new mutation upon antigen stimulation compared to responding B cells from young volunteers.

Figure 20:
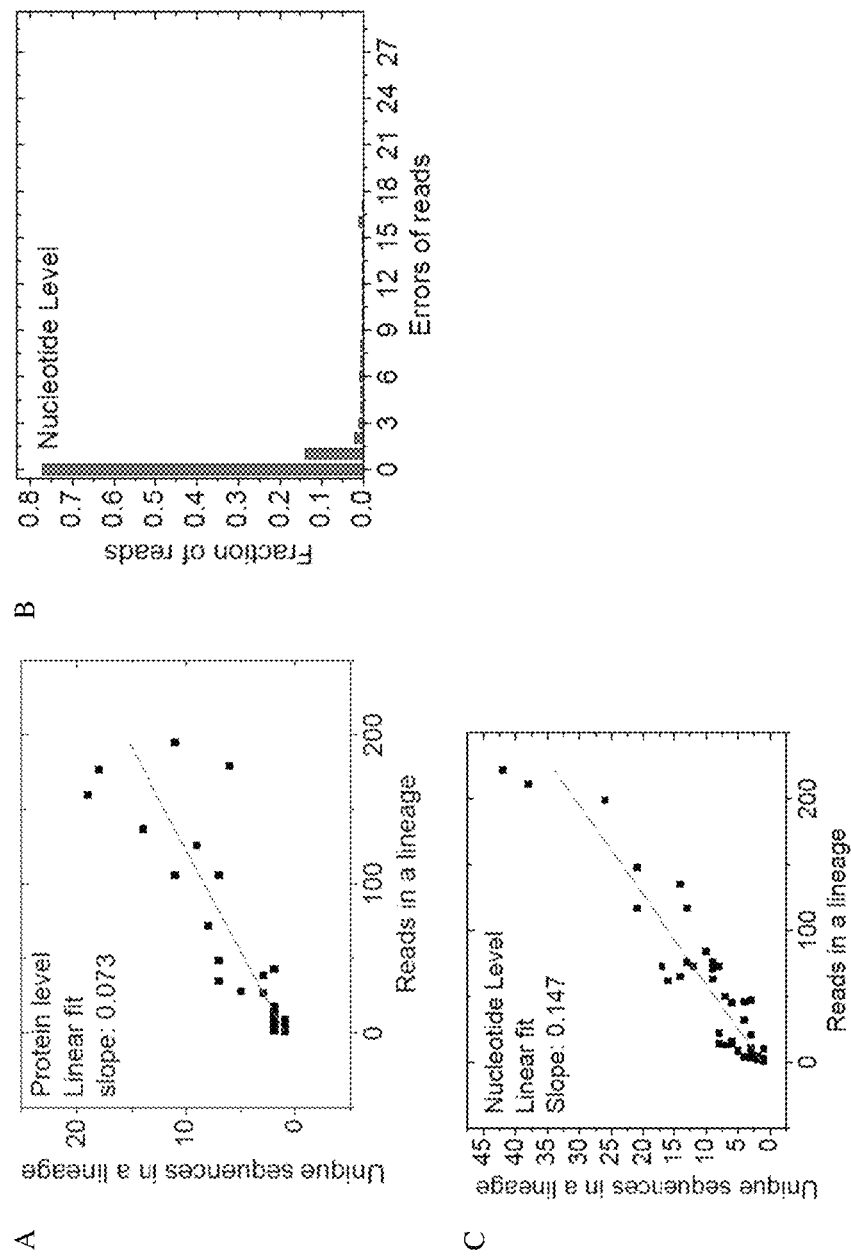
FIG. 20. Zebrafish control data. (A), relationship of number of reads and unique protein sequences in a cluster. Each data point is a cluster. The red line is the linear fit to the data. Clusters with more than 200 reads are excluded from this figure. (B), error rate profile of the control data at nucleotide level. The reference sequences are the most abundant sequence in each template. Indels are excluded (C), relationship of number of reads and unique nucleotide sequences in a cluster. Each data point is a cluster. The red line is the linear fit to the data.

In order to answer these questions, we performed a detailed analysis of mutation statistics. Although 454 sequencing has a high error rate, around 1%, most of them are insertions and deletions (indels) and can be repaired (FIG. 5). The substitution error rate (from sequencing and/or PCR) is estimated to be 0.065% per nucleotide (FIG. 20 and Control Library section). This is lower than the estimated somatic hypermutation rate, which is approximately 0.1% measured in nucleotides per cell division. Also, any B cells undergoing somatic hypermutation are likely to have several rounds of division, which increases their overall mutations per sequence. To analyze mutation statistics, we performed single linkage clustering by comparing the peptide sequences of CDR3 regions, using 1 amino acid as a threshold. We compared the average mutations-per-read from visit 1 PBMC across different age groups. This number consistently increased with age in the IgG fraction (FIG. 3B) while remaining at the background level and with no difference between age groups in the IgM fraction (FIG. 3C), which is consistent with the fact that most of the IgM expressing B cells are in a naïve state. We also applied the antibody-lineage clustering performed previously using junctional nucleotide sequences, thresholded at 80% identity.

We found that mutations in general are far higher in IgG than IgM, both when these mutations are measured relative to the germline reference sequences (FIGS. 3D and 3F) as well as to the most abundant sequence in each lineage. These observations point to mutational excursions of abundant class-switched sequences, as well as to diversification within the most abundant IgG lineages, respectively. In addition, there is a far greater parity between mutation-loads measured at visits 1 and 3 among IgM antibodies ($R^2=0.92$) than among IgG ($R^2=0.54$). In other words, even accounting for the variability amongst individuals, the IgM repertoire is more similar between before and after vaccine samples than the IgG repertoire. This demonstrates that IgG antibodies undergo a far greater change in composition between the two time points compared to IgM. Furthermore, the elderly had the highest number of amino acid mutations in both visit 1 and visit 3 IgG fraction (FIG. 3D) while remaining low and similar to the IgM fraction in both visits of other age groups (FIG. 3F). This trend is consistent with our mutation analysis using clustering performed on amino add sequences. IgG sequences had a higher number of mutations at visit 3 than visit 1 when these were tallied in reference to the most abundant sequence in each lineage (off diagonal line towards visit 3) suggesting that somatically hypermutated sequences persisted within the bloodstream 28 days after vaccination. At the same time, the elderly were not necessarily the group possessing the greatest number of mutations anymore relative to these most abundant sequences (FIG. 3E). Therefore, because they lack any indications of greater intraclonal mutation compared to other age-groups, these data suggest that the higher numbers of somatic mutations observed earlier in elderly individuals arise from clonal expansions that draw upon a pod of B-cells having more somatic mutations to begin with.

Although the antibody repertoire is encoded by gene segments that are common to each individual human being, the various processes of immunoglobulin diversity generation create a repertoire where the number of distinct immunoglobulin sequences in an individual exceeds the number of distinct genes in their consensus genome. The antibody repertoire is constantly evolving; it records the pathogenic exposure that one has experienced in the past and retains information on what it can protect us from. Therefore, it is of great interest to quantify and measure this dynamic system to understand how the repertoire responds to infection and vaccination and provide potential metrics for immune monitoring.

In this study, we used seasonal influenza vaccine as a means of stimulation, and measured and quantified the changes in the antibody repertoire. First, we observed that the relative percentage of IgM sequences dropped after vaccination across all volunteers except for one. This reduction in IgM usage decreased with age, which is consistent with the hypothesis that elderly are more likely to use memory B cells than naïve B cells to respond to influenza vaccination. We noted that children appear likely to increase relative IgA percentage in PBMCs compared to IgG.

A challenge of analyzing and quantifying the antibody repertoire is clonal expansion after antigen stimulation is not truly clonal as random mutations are introduced to the antibody genes at a rate of approximately $10^{-3}$ mutations per base pair per cell division. Using high-throughput sequencing in combination with informatics analysis, we were able to distinguish mutations, group sequences that differ by somatic hypermutation to the same clonal lineage, and follow the sequence evolution within a lineage. This approach enabled us an unbiased measurement of the relative size among different lineages within one individual and the sequence diversities within each lineage.

A network representation of lineages allowed visual comparison of the intricate intra- and inter-lineage structure. Many of the top lineages were composed of extensively connected CDR3 sequences, each with varying number of sequencing reads. Sequence data from our single cell cloning also confirmed that many of the top lineages are influenza specific (FIG. 2 and FIG. 15). Some single-cell-generated sequences did not have a high affinity towards any one of the virus strains used in the vaccine; it is possible that they may not be representative or the recombinant antibodies may have been specific to internal viral proteins rather than the whole virus used in the ELISA tests. The detailed topology of each lineage may contain information about how antigen selection and antibody affinity maturation work in concert in shaping the antibody repertoire. Studying the function of those informatically defined lineages may provide insight into this process.

Figure 23:
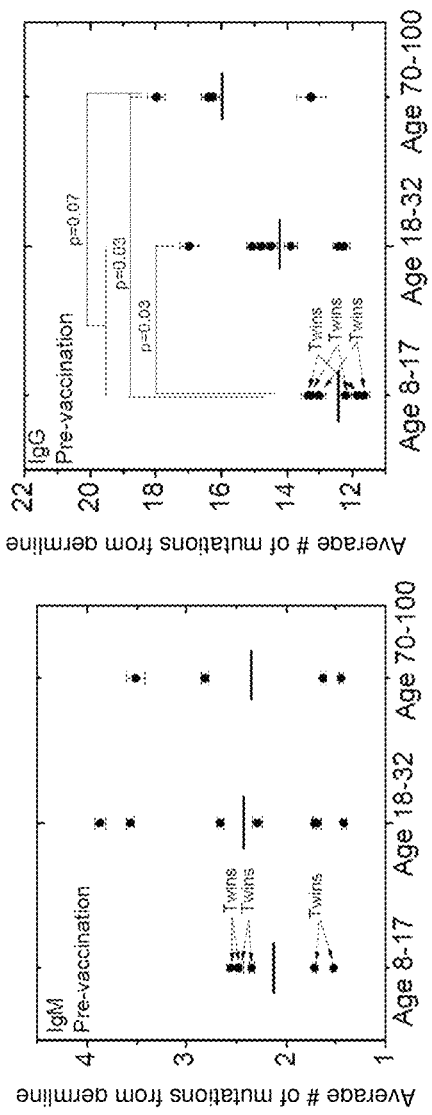
FIG. 23.

Having several twin pairs among our subjects provides an interesting genetic control for the data. As one might expect, for the IgM repertoire the twins have closely related mutational loads but these values diverge substantially for the IgG repertoire (FIG. 23). We attribute this to the notion that the naïve repertoire is probably more strongly influenced by the background genetics of the individual while the secondary repertoire incorporates a larger degree of stochasticity and randomness. The mutational load versus diversity graphs for twins show little correlation (FIG. 12, Age 8-17 group); this is also to be expected as these data represent strong environmental and stochastic contributions to the immune system.

In conclusion, we have shown that it is possible to make personalized individual-specific measurements of immune repertoire with high throughput DNA sequencing technology. These global repertoires contain a wealth of information and can be used to study individual-specific vaccine responses, and we have shown that analysis of the clonal structure provides direct insight into the effects of vaccination and provides a detailed molecular portrait of age-related effects. This approach to immune system characterization may be generally applicable to the development of new vaccines and may also help identify which individuals respond to a given vaccine.

Materials and Methods

Human participants, vaccination protocol, blood sample collection and cell sorting. Human participants, vaccination protocol, blood sample collection and cell sorting were described by Sasaki at al., Limited efficacy of inactivated influenza vaccine in elderly individuals is associated with decreased production of vaccine-specific antibodies. *J Clin Invest* 121, 3109 (2011). Samples from a subgroup of volunteers were used in this study and the demographical information of human participants was listed in Table 1. The study protocols were approved by the institutional review boards at Stanford University. Informed consent was obtained from participants and the parents of pediatric participants. In addition, assent was obtained from the child participants. Participants were immunized with one dose of either the 2009 or 2010 seasonal TIV (Fluzone, from Sanofi Pasteur) or LAIV (FluMist, from MedImmune). The 2009 vaccine contained an A/Brisbane/59/2007 (H1N1)-like virus, an A/Brisbane/10/2007 (H3N2)-like virus, and a B/Brisbane/60/2008-like virus. The 2010 vaccine contained an A/California/7/2009 (H1N1)-like virus, an A/Perth/16/2009 (H3N2)-like virus and a B/Brisbane/60/2008-like virus. Blood samples were collected from each participant at three time points: day 0 before vaccination, day 7 or 8, and day 28 (±4) after vaccination. PBMCs were isolated from the day 0 and day 28 blood samples using Ficoll-Paque Plus (GE Healthcare) following the manufacturer's instruction. Sorting of plasmablasts was performed as previously described (Sasaki, supra.) In brief, B-cells were isolated by negative selection using the RosetteSep Human B-cell Enrichment Cocktail (Stemcell Technologies) following the manufacturer's instructions from the day 7-8 whole blood samples. Plasmablasts were then sorted based on the phenotype of $CD3^-CD19^+CD20^-CD27^+CD38^+$ and naïve B cells were sorted based on the phenotype of $CD3^-CD19^+CD20^+CD27^-CD38^-$. Both populations reached a purity of 95%. Cells were lysed in RLT buffer (Qiagen) supplemented with 1% β-mercaptoethanol (Sigma) and stored at −80'C.

Primer design, RNA preparation, cDNA synthesis and PCR. 244 human heavy-chain variable gene segment sequences were downloaded from ImMunoGeneTics (IMGT), excluding pseudogenes. The leader regions of these sequences were used to design the 11 forward primers. The first 100 bp of the IgA, IgD, IgE, IgG and IgM constant domain were used to design the reverse primers. Gene specific primers were also designed for the reverse transcription step; these were located about 50 bp downstream from the PCR reverse primers. All primer sequences are listed in the Table 2.

10 million PBMCs or sorted cells with varying numbers lysed in RLT buffer was used as input material for RNA purification. This was done by using the All prep DNA/RNA purification kit (Qiagen) following manufacture's instruction. The concentration of the RNA was determined using a Nanodrop spectrophotometer.

cDNA was synthesized using SuperScrpt™ III reverse transcriptase (Invitrogen). One fifth of the RNA purified from each sample was used for cDNA synthesis reactions with a total volume of 60 ul. All five constant region reverse transcription primers were added to the same reaction together with SUPERase•In™ (Ambion). RNase H (Invitrogen) was added to each reaction to remove RNA at the end of the cDNA synthesis step. All enzyme concentrations, reaction volumes and the incubation temperature were based on the manufacturer's protocol for synthesis of cDNA using gene specific primers.

For each sample, 11 PCR reactions were set up corresponding to 11 forward primers with a mixture of 5 reverse primers in each reaction. 2 μl of reverse transcription mixture was used in each PCR reaction of 50 μl. Final concentration of 200 nM was used for each primer. The PCR program began with an initial denaturation at 94° C. for 2 minutes, followed by 35 cycles of denaturation at 94° C. for 30 s, annealing of primer to DNA at 50° C. for 30 s, and extension by Platinum® Taq DNA Polymerase High Fidelity (Invitrogen) at 68° C. for 2 minutes. PCR products were first cleaned using QIAquick PCR Purification Kit (Qiagen) and then purified using the QIAquick gel extraction kit (Qiagen). Concentration was measured using the nanodrop spectrophotometer.

454 library preparation and sequencing. About 0.5 μg of QIAquick cleaned PCR product for each sample was used to start the 454 library preparation process. 454 Titanium shotgun library construction protocol was followed for all samples. Briefly, double stranded DNA was end polished and ligated to sequencing adaptors which contained a molecular identifier (MID, a nucleotide based barcode system). The rest of the Roche 454 protocol was followed which includes library immobilization, fill-in reaction and single stranded template DNA (sstDNA) library isolation. The sstDNA was quantified using a digital-PCR method, White et al, Digital PCR provides sensitive and absolute calibration for high throughput sequencing. *BMC Genomics* 10, 116 (2009). Up to 16 libraries were pooled for one sequencing run and Roche 454 emulsion PCR and sequencing protocols were followed for the rest of the sequencing procedure.

Data Analysis.

Figure 6I:
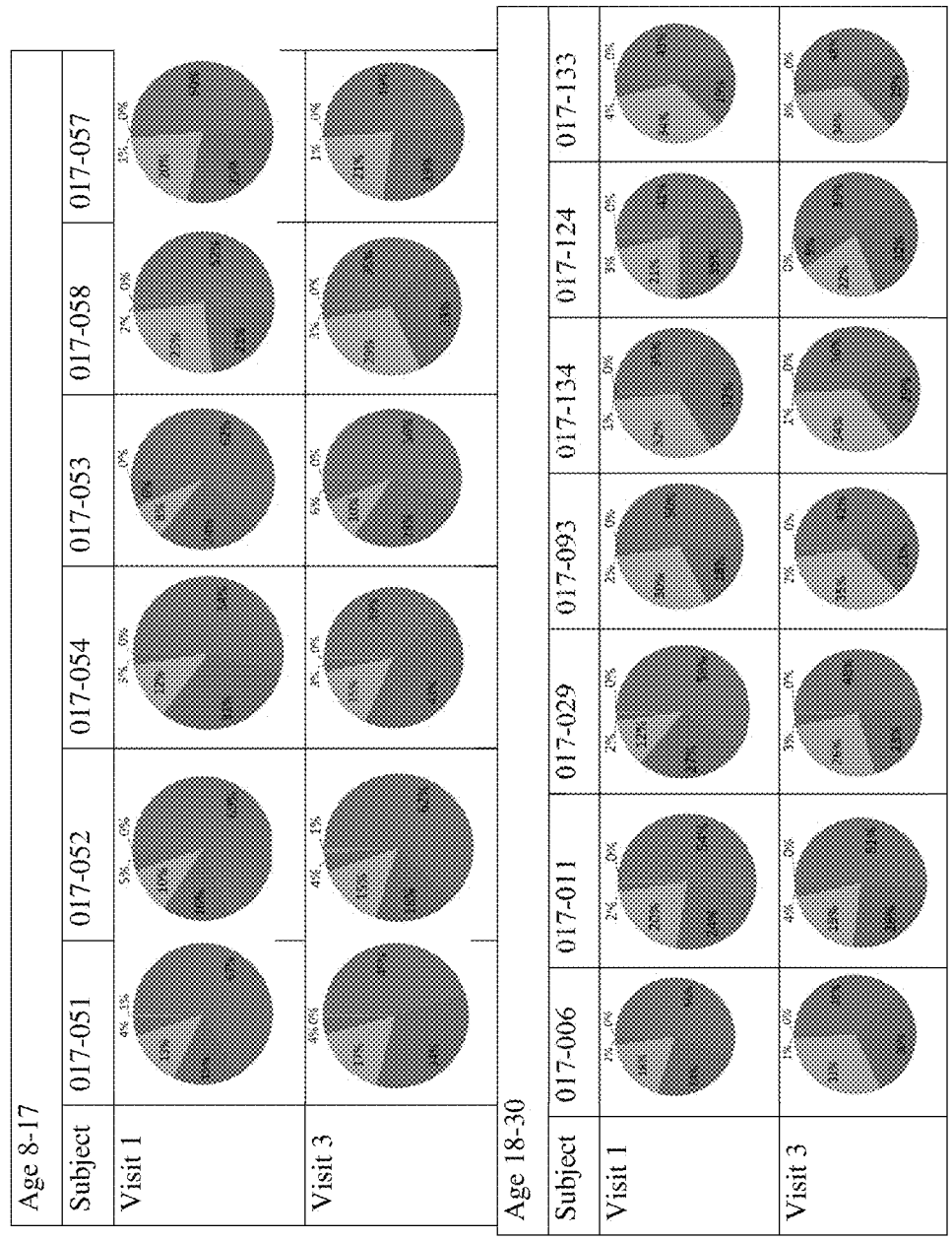
FIGS. 6i and 6ii. The composition of five antibody isotypes from PBMCs for each subject at visits 1 and 3. The percentage of an isotype in a subject was calculated using the number of reads within a particular isotype divided by the total number of reads of this sample. Reads from a subset of runs were used. 3000 reads of subsampling was not applied here.
Figure 6I:
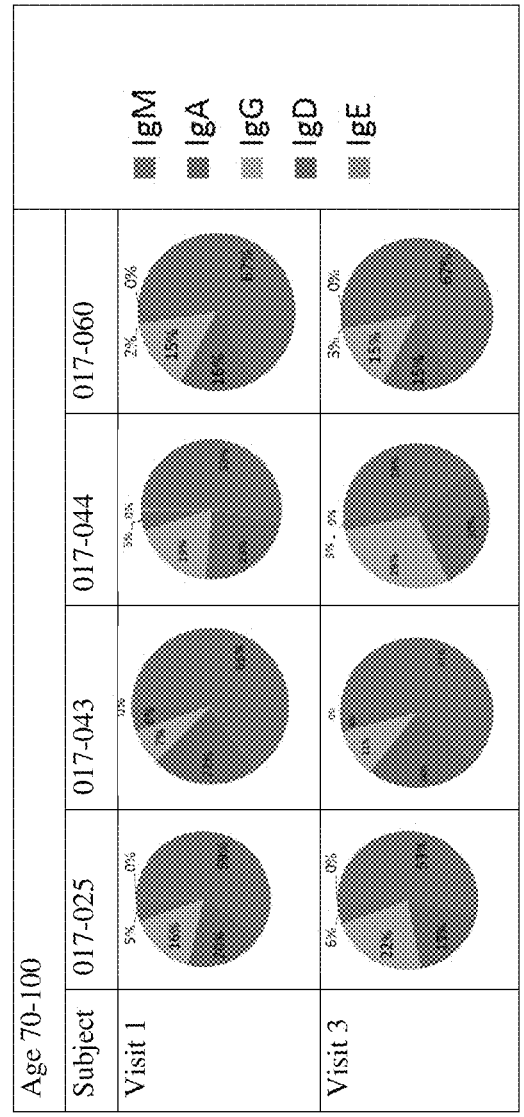

Primary sequencing reads processing. Reads from Roche 454 entered into the primary analysis; see the flowchart in FIG. 5. Only those reads that matched exactly to the corresponding sample's MID code were included for further process. These reads were then filtered for a minimum length of 250 bp, see Table 3 for filtered reads number for each sample. Longer reads were truncated to this length. Only these reads were considered for the rest of the analysis. The isotype of each read was identified by the reverse primer at the constant region; see FIG. 6 for isotype composition.

Isotype class switch. One important process of affinity maturation is isotype switching. The naïve B cells are mostly expressing IgM and they undergo isotype switching from IgM to IgG, IgA or IgE after antigen stimulation and proliferation. We explicitly verified the presence of isotype switching in the sequence data by taking a closer look at the lineages in the plasmablasts for each subjects. We re-performed the clustering analysis on pooled IgM and IgG sequences and allow both isotypes to join the same lineage as long as their CDR3 region satisfied the predetermined criteria, which is 1 amino acid difference. Here, we consider a lineage is isotype switched, if both IgM and IgG sequences are observed in the lineage. Elderly have less isotype switched lineages than that of children (see FIG. 8). We observed only a few cases where the identical variable region can be found in both IgG and IgM isotypes. But for most of the cases, extensive mutations also occurred throughput the variable region as exemplified in FIG. 9.

VDJ classification. Human heavy-chain variable gene segment sequences (244 V-exon, 37 D-exon and 13 J-exon) were downloaded from the International ImMunoGeneTics information system database (Giudicelli, et al., IMGT/GENE-DB: a comprehensive database for human and mouse immunoglobulin and T cell receptor genes. *Nucleic Acids Res* 33, D256 (2005)), excluding pseudogenes. These germline sequence templates of V and J can be grouped by combining alleles into subclasses. In total, 63 V and 7 J subclasses were obtained. D-exons were not grouped because they are highly diversified. Each read was first aligned to V-consensus sequences taken over each V-family. The specific V-variant with a maximum Smith-Waterman score (Jiang et al., Determinism and stochasticity during maturation of the zebrafish antibody repertoire. *Proc Natl Acad Sci USA* 108, 5348 (2011)) was then assigned. J-segments (out of 13 variants) and D-segments (out of 37) were then assigned as described, with ambiguous D-segments given their own class. Grouping each V, D, and J gene assignment into subclasses gave the total number of possible VDJ subclass assignments of 63 (V)×37 (D)×7 (J)=16317 (VDJ). The mutation from germline sequence was counted as the number of substitutions from the best aligned V, C and J templates. Unaligned region at the VD and DJ junctions was excluded from the mutation count.

Translation from nucleotide to amino acid sequences. Nucleotide sequences were translated into amino acid sequences based on codon translation (see the flowchart in FIG. 5). We used the amino acid sequences in the IMGT database as the reference to detect the correct translation frame in the V region. If the reading frame was correct at the constant region, the translation was accepted for further analysis. Since the dominant sequencing error in 454 Roche platform is insertion and deletion, if the translation was out of frame at the constant region, we performed sequence translation rescue. We deleted all insertions and filled the deletions by the corresponding nucleotide base in the germline sequences, and performed a second translation. If the second translation had the correct reading frame at the constant region, the rescue was successful and the protein sequence from the second translation was accepted for further analysis, otherwise, the sequence was discarded. About 12% of reads were discarded. CDR3 region detection was based on two sequence markers. The boundary of CDR3 is defined by amino acid sequence from 'tyr-(tyr/phe)-cys' to 'trp-gly' (Kabat et al., Sequences of Proteins of Immunological Interest, (Public Health Service, National Institutes of Health, Washington, D.C., ed. 5, 1991), vol. 1.).

Protein distance analysis. Protein distance analysis is a way to caption overall relationship of proteins in the entire repertoire. The CDR3 sequence difference $d_{ij}$ was defined as the hamming distance between protein sequence i and protein sequence j in the CDR3 region. We used the minimum distance of sequence i to other sequences in the same sample, formally:

$$\bar{d}_i = \min(d_{ij}, j=1, 2 \ldots N)$$

The VD junction and DJ junction regions are around 15 nucleotide bases long in total, therefore, two sequences with the same VDJ assignment but from independent VDJ recombination event may differ by 5 amino acids ($d_{ij} \approx 5$). The hypermutation rate is estimated to between $10^{-3}$ and $10^{-4}$ per base pair per generation and the average CDR3 length is 58 bp, thus, two sequences that differ by one amino acid at the CDR3 are likely from the descents of the same naïve B cell.

CDR3 distance distribution. In order to study the relative distance between any two sequence read, we performed the following analysis on amino acid sequences following the scheme described in FIG. 5. We first catalog amino acid difference in the CDR3 region between any two sequencing reads, which can be as small as 1 amino add or as large as 18 amino adds, and grouped sequencing reads according to this difference. If a sequence can be grouped to several groups following this difference, then this sequence will be assigned to a group with minimum amino acid difference. Resulted distribution showed two distinct peaks, one is at 1 amino add and the other expands 4 to 10 amino adds, as observed in FIG. 10. This distribution provided us a guideline to set the threshold when clustering was used as a way to group sequences into lineages.

Clustering Sequences into Clonal lineages. Sequences with similar CDR3 are possible progenies from the same naïve B cell and can be grouped into the same clonal lineage. To detect the lineage structure for the antibody repertoire, we performed single linkage clustering on protein sequences of CDR3 region, using a re-parameterization of the method described in Jiang et al 2011, accounting for the larger size of the CDR3 and junction in humans as compared to zebrafish. Protein sequences with the same V and J assignment and with CDR3 region differed by no more than one amino add were grouped together into a lineage. This is equivalent to a biological clone that is under clonal expansion. The diversity of a lineage or a sample was defined as the number of unique sequences within the lineage or the sample, after grouping identical reads.

Lineage structure of antibody repertoire. After grouping reads into lineages, we can take a detailed look of inter- and intra-lineage structure for a sample as exemplified in FIGS. 2 and 4, and FIG. 11-14. In FIG. 12, the lineage structure of plasmablasts of all subjects in visit 2 were displayed in reference to mutation, diversity and reads of a lineage. In two of the elderly individuals (017-060 and 017-043), we observed dominant lineages that account for 49% of all reads observed in those samples. We performed the same lineage structure analysis for individual 017-060 in visit 1. The dominant lineage of 017-060 at visit 2 was not observed in visit 1.

Lineage structure of naïve B cells. Lineage structure of naïve B cells and plasmablasts from the same subject were studied. The naïve B cells are dominant by single-read clusters without mutations from germline sequences while plasmablasts contain many lineages with varying amount of sequencing reads and mutations (see FIG. 11).

Antibody abundance distribution. The majority of the lineages contain only one reads, however, a few lineages are highly abundant. The distribution of lineage size of plasmablasts follows power law with the exponent of power −1.7 (FIG. 17). There is no highly abundant lineage in naïve B cells and this can be explained by the fact that naïve B cells are not stimulated and have not undergone clonal expansion.

Figure 18:
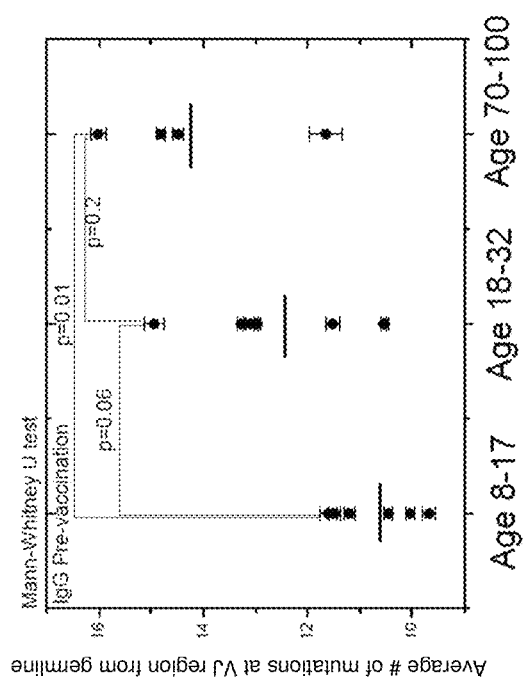
FIG. 18. Mutation pattern of IgG for three age groups in visit 1 PBMCs. The number of mutations for each read was defined as the number of mismatches to germline reference in V and J region. 3000 reads of subsampling was applied to this figure. All error bars are standard error.

Mutation in V and J region. It is concerned that the mutation in D region is unreliable, because the alignment of D region to germline reference could be ambiguous. Here, we demonstrate that the mutation pattern of different age groups in visit 1 PBMC is similar whether mutation in D region is counted or not (FIG. 18). The trend of mutation pattern is the same if one compares FIG. 18 to FIG. 3B.

Varying clustering threshold. In the FIG. 2-4, the single linkage clustering was performed with the threshold of one amino acid difference in the CDR3 region. Here, we show that the mutation patterns remain the same under different clustering thresholds.

Control Data

Control library. Control experiments were performed by a mixture of cloned zebra fish immunoglobulin genes that covered all possible V gene segments (11, 15). Briefly, 38 immunoglobulin genes for IgM containing different V gene segments were cloned into plasmid and sequenced using Sanger sequencing. To quantitatively measure the PCR bias and sequencing errors, plasmids containing 38 clones were pooled. Part of the pooled material went through the same PCR cycle as human samples and part of the pooled material was not PCR amplified. 454 libraries were made using these two sets of materials and sequenced using 454. The degree of error introduced in the sample amplification and sequencing process was estimated by comparing these two sets of control libraries to the most abundant sequence for each template.

Figure 21:
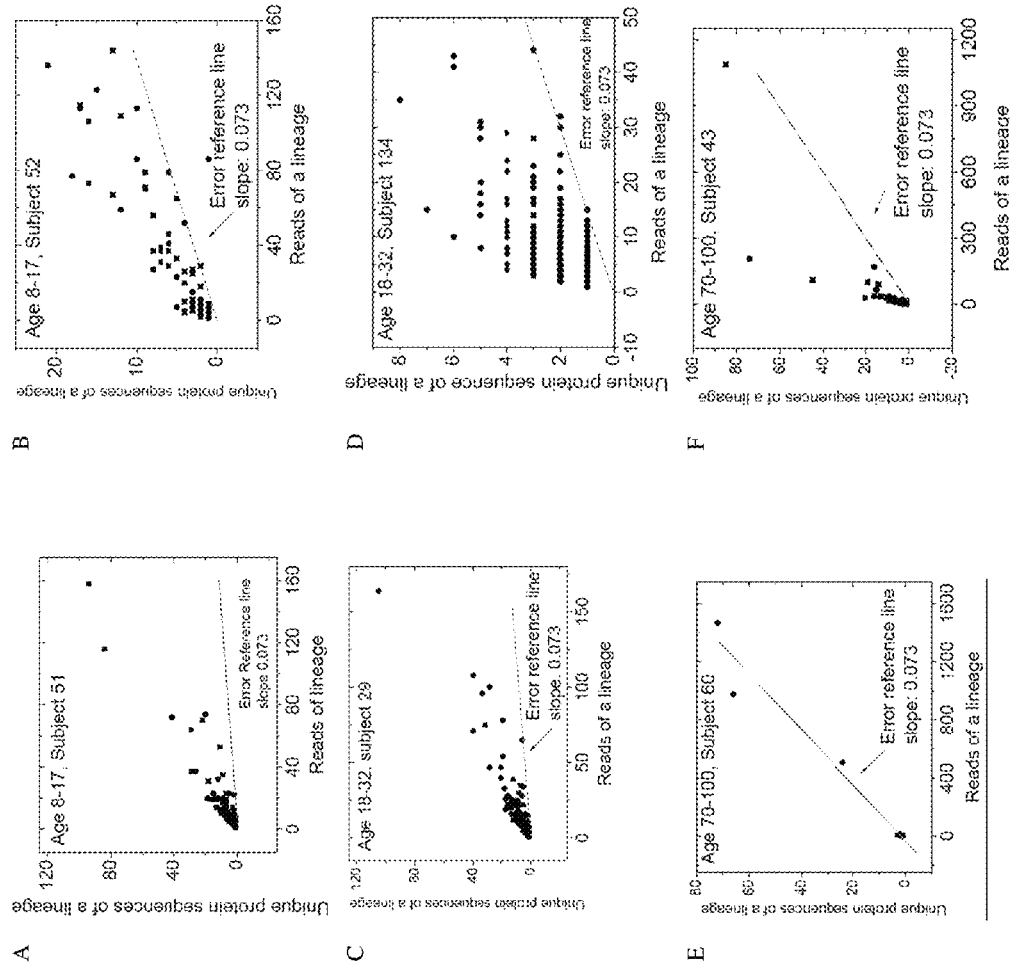
FIG. 21A-F. Diversity and reads of IgG lineages of human plasmablasts at visit 2. Each dot in the figures is a lineage. X- and Y-axis are reads and unique protein sequences of the lineage respectively. The blue line is the expected diversity from zebrafish control data. The slope, 0.073, was estimated from Supplementary FIG. 16A.

The most abundant sequence from each template was chosen to be the reference sequence. Each 454 read was aligned to these reference sequences. All reads were translated into protein sequence and translation rescue was performed as well. As a result, this corrected most of the insertion and deletions which is the most common error for 454 sequencing. Following analysis is focus on substitution errors from PCR and sequencing. 77% sequence reads are error-free in their entire 220 bp nucleotide sequence (with 30 bp from the MID barcode and primer being excluded) and 13.6% sequence reads has one substitution (FIG. 20B). The substitution error rate was estimated to be 0.065% per bp (detectable chimeras were excluded). Single lineage clustering is performed on nucleotide sequences. Linear relationship between reads in a lineage and unique sequences in a lineage is observed with a slope of 0.147 in the fig. S16C, in agreement with fraction of one-substitution reads. We also did single lineage clustering in protein level and observed a slop of 0.073 in the FIG. 20A. In the human data, the diversity is usually higher than what is estimated from substitution error (FIG. 21), if the human data is assumed to have the same error profile as zebrafish control data. In most of the subjects, the real sequences are much more than "artificial sequences" created from substitution errors.

Figure 22:
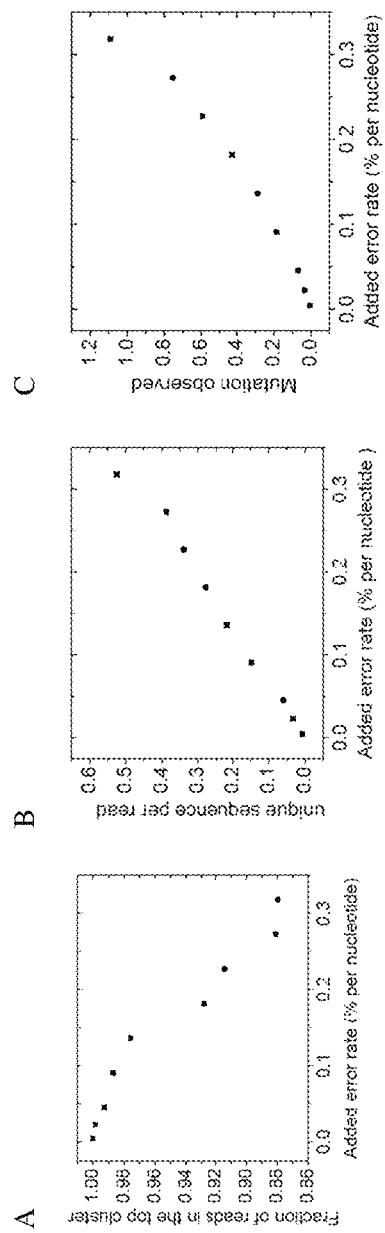
FIG. 22. Synthetic sequence control data. (A), the fraction of reads in the largest cluster is linearly proportional to the added error rate. (B), added errors increase the diversity. (C), added errors increase the mutation from baseline. Each data point is an independent trial.

Synthetic control data. To test the reliability of our analysis pipelines, we constructed synthetic control data and processed the synthetic data using the same pipeline that was used on human data. The synthetic control data was generated from a single sequence with 3000 reads. The sequence was a randomly selected IgG heavy chain from one subject. Errors were added to the sequence reads to mimic the substitution errors. Each base of each reads was given a constant probability to be changed to another random nucleotide. Therefore, error rate in the synthetic control data was a predefined parameter and was indicated on the X-axis. The range tested is within the estimated substitution rate of 454 sequencing platform. The analysis showed that sequences included in the largest cluster linearly decrease with the error rate and the number of unique sequences linearly increase with error rate. The mutation from baseline also linearly depended on the error rate (FIG. 22).

TABLE 1

Demographical information of human participants.

| Patient ID | Age | Vaccine year | Vaccine | twin-status |
|---|---|---|---|---|
| 017-006 | 18-30 | 2009 | TIV | NA |
| 017-011 | 18-30 | 2009 | TIV | NA |
| 017-029 | 18-30 | 2009 | TIV | NA |
| 017-025 | 70-100 | 2009 | TIV | NA |
| 017-043 | 70-100 | 2009 | TIV | NA |
| 017-044 | 70-100 | 2009 | TIV | NA |

TABLE 1-continued

Demographical information of human participants.

| Patient ID | Age | Vaccine year | Vaccine | twin-status |
|---|---|---|---|---|
| 017-060 | 70-100 | 2009 | TIV | NA |
| 017-051 | 8-17 | 2009 | TIV | twin with 052 |
| 017-052 | 8-17 | 2009 | LAIV | twin with 051 |
| 017-053 | 8-17 | 2009 | LAIV | twin with 054 |
| 017-054 | 8-17 | 2009 | TIV | twin with 053 |
| 017-057 | 8-17 | 2009 | LAIV | twin with 058 |
| 017-058 | 8-17 | 2009 | TIV | twin with 057 |
| 017-134 | 18-30 | 2010 | LAIV | NA |
| 017-124 | 18-30 | 2010 | LAIV | NA |
| 017-133 | 18-30 | 2010 | TIV | NA |
| 017-093 | 18-30 | 2010 | TIV | NA |

TABLE 2

Primer sequences.

| | | SEQ ID NO |
|---|---|---|
| PCR forward primers | | |
| LR1 | CGCAGACCCTCTCACTCAC | 1 |
| LR2 | TGGAGCTGAGGTGAAGAAGC | 2 |
| LR3 | TGCAATCTGGGTCTGAGTTG | 3 |
| LR4 | GGCTCAGGACTGGTGAAGC | 4 |
| LR5 | TGGAGCAGAGGTGAAAAAGC | 5 |
| LR6 | GGTGCAGCTGTTGGAGTCT | 6 |
| LR7 | ACTGTTGAAGCCTTCGGAGA | 7 |
| LR8 | AAACCCACACAGACCCTCAC | 8 |
| LR9 | AGTCTGGGGCTGAGGTGAAG | 9 |
| LR10 | GGCCCAGGACTGGTGAAG | 10 |
| LR11 | GGTGCAGCTGGTGGAGTC | 11 |
| PCR reverse primers | | |
| IgG-PCR | AAGACCGATGGGCCCTTG | 12 |
| IgA-PCR | GAAGACCTTGGGGCTGGT | 13 |
| IgM-PCR | GGGAATTCTCACAGGAGACG | 14 |
| IgE-PCR | GAAGACGGATGGGCTCTGT | 15 |
| IgD-PCR | GGGTGTCTGCACCCTGATA | 16 |
| Reverse transcription primers | | |
| IgG-RT | GGGAAGTAGTCCTTGACCAG | 17 |
| IgA-RT | GGGGAAGAAGCCCTGGAC | 18 |
| IgM-RT | GGCCACGCTGCTCGTATC | 19 |
| IgE-RT | AGGGAATGTTTTTGCAGCAG | 20 |
| IgD-RT | CCACAGGGCTGTTATCCTTT | 21 |

TABLE 3

Summary of cell numbers and filtered reads for all samples.

| Subject ID | Visit 1 PBMC (reads) | Visit 2 Naïve B cells (reads) | Visit2 Naïve B cell # | Visit 2 Plasmablasts (reads) | Visit 2 Plasmablasts # | Visit 3 PBMC (reads) | Visit 2 PBMC (reads) |
|---|---|---|---|---|---|---|---|
| 017-006 | 18370 | 251140 | 88576 | 25356 | 12557 | 23743 | N/A |
| 017-011 | 112250 | 59494 | 10467 | 51575 | 1847 | 40451 | N/A |
| 017-029 | 29134 | 81014 | 39502 | 82336 | 46135 | 288484 | N/A |
| 017-025 | 66900 | 42305 | 8453 | 83360 | 3100 | 84739 | N/A |
| 017-043 | 3949 | 66050 | 66472 | 25290 | 33455 | 35149 | N/A |
| 017-044 | 31467 | 18638 | 23974 | 24492 | 8402 | 26262 | N/A |
| 017-060 | 33560 | 26538 | 29361 | 14421 | 3346 | 26769 | N/A |
| 017-051 | 51442 | 61240 | 189294 | 63736 | 156019 | 100499 | N/A |
| 017-054 | 62117 | 51034 | 61915 | 98952 | 78264 | 51243 | N/A |
| 017-052 | 95625 | 57756 | 86783 | 56080 | 6501 | 64980 | N/A |

TABLE 3-continued

Summary of cell numbers and filtered reads for all samples.

| Subject ID | Visit 1 PBMC (reads) | Visit 2 Naïve B cells (reads) | Visit2 Naïve B cell # | Visit 2 Plasmablasts (reads) | Visit 2 Plasmablasts # | Visit 3 PBMC (reads) | Visit 2 PBMC (reads) |
|---|---|---|---|---|---|---|---|
| 017-053 | 35488 | 40826 | 50815 | 27124 | 126634 | 28840 | N/A |
| 017-058 | 10926 | 11869 | 29332 | 15956 | 10758 | 20180 | N/A |
| 017-057 | 28584 | 25628 | 28313 | 28544 | 13648 | 23884 | N/A |
| 017-093 | 34364 | 91 | 100000 | 15574 | 5000 | 32417 | 28700 |
| 017-134 | 45987 | 73627 | 118000 | 113360 | 8600 | 32296 | 59247 |
| 017-124 | 16127 | 35672 | 124000 | 13040 | 27000 | 27887 | 27008 |
| 017-133 | 33547 | 42297 | 28000 | 13183 | 36000 | 29806 | 26531 |
| Average | 41755 | 55601 | | 44257 | | 55154 | 32506 |

TABLE 4

Raw reads for five isotypes in each sample. Reads from a subset of runs were used.

| subject | | | IgM | IgA | IgG | IgD | IgE | Isotype identifiable |
|---|---|---|---|---|---|---|---|---|
| 52 | visit 2 | Plasmablasts | 6862 | 21998 | 26422 | 163 | 635 | 56080 |
| 53 | visit 2 | Plasmablasts | 3023 | 5446 | 12349 | 3 | 148 | 20969 |
| 51 | visit 2 | Plasmablasts | 6859 | 16742 | 39813 | 50 | 272 | 63736 |
| 54 | visit 2 | Plasmablasts | 18005 | 20555 | 60055 | 5 | 332 | 98952 |
| 57 | visit 2 | Plasmablasts | 2280 | 12312 | 13937 | 15 | 0 | 28544 |
| 58 | visit 2 | Plasmablasts | 1507 | 2902 | 11539 | 8 | 0 | 15956 |
| 6 | visit 2 | Plasmablasts | 2687 | 7749 | 14890 | 0 | 30 | 25356 |
| 11 | visit 2 | Plasmablasts | 4591 | 17676 | 28546 | 499 | 263 | 51575 |
| 29 | visit 2 | Plasmablasts | 24728 | 15764 | 41613 | 4 | 227 | 82336 |
| 134 | visit 2 | Plasmablasts | 19983 | 44492 | 48333 | 72 | 480 | 113360 |
| 93 | visit 2 | Plasmablasts | 2553 | 4356 | 8401 | 58 | 206 | 15574 |
| 124 | visit 2 | Plasmablasts | 1124 | 6702 | 5186 | 18 | 10 | 13040 |
| 133 | visit 2 | Plasmablasts | 331 | 2221 | 10620 | 0 | 11 | 13183 |
| 25 | visit 2 | Plasmablasts | 6343 | 31777 | 43851 | 784 | 605 | 83360 |
| 43 | visit 2 | Plasmablasts | 1535 | 126 | 23615 | 3 | 11 | 25290 |
| 44 | visit 2 | Plasmablasts | 1688 | 526 | 22268 | 10 | 0 | 24492 |
| 60 | visit 2 | Plasmablasts | 150 | 8244 | 6022 | 2 | 3 | 14421 |
| 6 | visit 1 | PBMC | 10235 | 4389 | 3324 | 415 | 7 | 18370 |
| 11 | visit 1 | PBMC | 60684 | 26467 | 22410 | 2600 | 89 | 112250 |
| 25 | visit 1 | PBMC | 39665 | 12934 | 10734 | 3557 | 10 | 66900 |
| 29 | visit 1 | PBMC | 17189 | 7875 | 3440 | 501 | 129 | 29134 |
| 43 | visit 1 | PBMC | 2999 | 70 | 583 | 296 | 1 | 3949 |
| 44 | visit 1 | PBMC | 19177 | 401 | 9972 | 1859 | 58 | 31467 |
| 52 | visit 1 | PBMC | 65497 | 15315 | 10016 | 4746 | 51 | 95625 |
| 53 | visit 1 | PBMC | 11456 | 4443 | 1558 | 1177 | 4 | 18638 |
| 60 | visit 1 | PBMC | 22447 | 5302 | 5001 | 791 | 19 | 33560 |
| 57 | visit 1 | PBMC | 14223 | 8256 | 5744 | 355 | 6 | 28584 |
| 93 | visit 1 | PBMC | 17092 | 6199 | 10182 | 875 | 16 | 34364 |
| 133 | visit 1 | PBMC | 14570 | 6350 | 11402 | 1187 | 38 | 33547 |
| 134 | visit 1 | PBMC | 15961 | 14550 | 14732 | 725 | 19 | 45987 |
| 124 | visit 1 | PBMC | 6522 | 5616 | 3436 | 525 | 28 | 16127 |
| 58 | visit 1 | PBMC | 5652 | 2315 | 2714 | 242 | 3 | 10926 |
| 51 | visit 1 | PBMC | 34254 | 7897 | 6680 | 2163 | 448 | 51442 |
| 54 | visit 1 | PBMC | 33666 | 19360 | 7492 | 1562 | 37 | 62117 |
| 6 | visit 3 | PBMC | 8961 | 7204 | 7310 | 233 | 35 | 23743 |
| 11 | visit 3 | PBMC | 20428 | 10671 | 7870 | 1465 | 17 | 40451 |
| 25 | visit 3 | PBMC | 45215 | 15842 | 18957 | 4653 | 72 | 84739 |
| 29 | visit 3 | PBMC | 138619 | 65065 | 74933 | 9350 | 517 | 288484 |
| 43 | visit 3 | PBMC | 25903 | 318 | 6981 | 1939 | 8 | 35149 |
| 44 | visit 3 | PBMC | 12498 | 327 | 12349 | 990 | 98 | 26262 |
| 52 | visit 3 | PBMC | 40503 | 11625 | 9433 | 2625 | 794 | 64980 |
| 53 | visit 3 | PBMC | 11589 | 5926 | 2046 | 1193 | 10 | 20764 |
| 60 | visit 3 | PBMC | 17947 | 4098 | 3890 | 817 | 17 | 26769 |
| 57 | visit 3 | PBMC | 11575 | 6951 | 5058 | 280 | 20 | 23884 |
| 93 | visit 3 | PBMC | 13571 | 6890 | 11177 | 762 | 17 | 32417 |
| 133 | visit 3 | PBMC | 11291 | 7389 | 10296 | 813 | 17 | 29806 |
| 134 | visit 3 | PBMC | 11613 | 9220 | 11120 | 336 | 7 | 32296 |
| 124 | visit 3 | PBMC | 10979 | 8329 | 6016 | 2542 | 21 | 27887 |
| 58 | visit 3 | PBMC | 7098 | 6657 | 5850 | 567 | 8 | 20180 |
| 51 | visit 3 | PBMC | 45315 | 34524 | 16452 | 4022 | 186 | 100499 |
| 54 | visit 3 | PBMC | 19909 | 22037 | 7655 | 1496 | 146 | 51243 |
| 134 | visit 2 | Naïve B cells | 65372 | 2310 | 4150 | 1633 | 162 | 73627 |
| 93 | visit 2 | Naïve B cells | 90 | 0 | 1 | 0 | 0 | 91 |
| 124 | visit 2 | Naïve B cells | 32776 | 737 | 1328 | 826 | 5 | 35672 |
| 133 | visit 2 | Naïve B cells | 37141 | 1247 | 2919 | 952 | 38 | 42297 |

TABLE 4-continued

Raw reads for five isotypes in each sample. Reads from a subset of runs were used.

| subject | | | IgM | IgA | IgG | IgD | IgE | Isotype identifiable |
|---|---|---|---|---|---|---|---|---|
| 6 | visit 2 | Naïve B cells | 209550 | 12793 | 24457 | 3722 | 618 | 251140 |
| 11 | visit 2 | Naïve B cells | 48579 | 1155 | 2884 | 5956 | 920 | 59494 |
| 29 | visit 2 | Naïve B cells | 57741 | 6148 | 9659 | 6028 | 1438 | 81014 |
| 25 | visit 2 | Naïve B cells | 31518 | 1885 | 3631 | 3199 | 2072 | 42305 |
| 43 | visit 2 | Naïve B cells | 60009 | 47 | 850 | 5117 | 27 | 66050 |
| 44 | visit 2 | Naïve B cells | 13576 | 154 | 3149 | 1739 | 20 | 18638 |
| 60 | visit 2 | Naïve B cells | 24717 | 91 | 1129 | 576 | 25 | 26538 |
| 51 | visit 2 | Naïve B cells | 35896 | 5872 | 13164 | 4887 | 1421 | 61240 |
| 52 | visit 2 | Naïve B cells | 46047 | 2106 | 3220 | 5584 | 799 | 57756 |
| 53 | visit 2 | Naïve B cells | 16385 | 2127 | 2410 | 1208 | 38 | 22168 |
| 54 | visit 2 | Naïve B cells | 35615 | 2039 | 8639 | 3917 | 824 | 51034 |
| 57 | visit 2 | Naïve B cells | 23952 | 455 | 549 | 594 | 78 | 25628 |
| 58 | visit 2 | Naïve B cells | 10281 | 219 | 698 | 665 | 6 | 11869 |

TABLE 5

Summary of identifiable VJ reads for IgG in visit 2 plasmablasts.

| Subject ID | Identifiable IgG VJ reads | Raw IgGreads | Fraction of identifiable VJ reds |
|---|---|---|---|
| 51 | 39389 | 39813 | 0.98935 |
| 54 | 59465 | 60055 | 0.990176 |
| 53 | 21127 | 21367 | 0.988768 |
| 58 | 11528 | 11539 | 0.999047 |
| 57 | 13870 | 13937 | 0.995193 |
| 29 | 41165 | 41613 | 0.989234 |
| 6 | 14772 | 14890 | 0.992075 |
| 25 | 42072 | 43851 | 0.959431 |
| 43 | 23608 | 23615 | 0.999704 |
| 44 | 22222 | 22268 | 0.997934 |
| 60 | 6010 | 6022 | 0.998007 |
| 11 | 27883 | 28546 | 0.976774 |
| 52 | 24693 | 26422 | 0.934562 |
| 134 | 48024 | 48333 | 0.993607 |
| 93 | 8376 | 8401 | 0.997024 |
| 124 | 5173 | 5186 | 0.997493 |
| 133 | 10605 | 10620 | 0.998588 |

TABLE 6

Summary of single cell cloned sequences.

| antibody | identical AA sequences in visit 2 PB (excluding itself) | unique AA sequences in the cluster (excluding itself) in visit 2 PB | reads of the SCC containing cluster (including itself) in visit 2 PB | Mutation (nt) of SCC antibody | Minimum mutation (nt) of the SCC containing cluster in visit 2 PB | Maximum mutation (nt) of the SCC containing cluster in visit 2 PB | SCC sequence Binding to antigen? | Unique AA sequences in the cluster (excluding itself) in visit 3 PBMC |
|---|---|---|---|---|---|---|---|---|
| subject 017-043 | | | | | | | | |
| A06 | 0 | 0 | 1 | 8 | 8 | 8 | N | 0 |
| B03 | 3764 | 427 | 6884 | 7 | 3 | 15 | N | 1 |
| C02 | 0 | 4 | 38 | 9 | 9 | 12 | Y | 1 |
| C06 | 43 | 427 | 6884 | 8 | 3 | 15 | N | 1 |
| D06 | 5 | 427 | 6884 | 13 | 3 | 15 | N | 1 |
| E04 | 0 | 541 | 2599 | 39 | 14 | 40 | Y | 0 |
| E05 | 207 | 427 | 6884 | 8 | 3 | 15 | N | 1 |
| E06 | 70 | 427 | 6884 | 7 | 3 | 15 | N | 1 |
| F06 | 1 | 7 | 59 | 14 | 14 | 18 | Y | 17 |
| G04 | 0 | 0 | 1 | 12 | 12 | 12 | N | 0 |
| subject 017-044 | | | | | | | | |
| B01 | 0 | 5 | 22 | 22 | 18 | 29 | N | 0 |
| B03 | 0 | 0 | 1 | 7 | 7 | 7 | N | 0 |
| C05 | 0 | 11 | 103 | 24 | 24 | 28 | Y | 0 |
| C06 | 0 | 0 | 1 | 25 | 25 | 25 | Y | 0 |
| D02 | 0 | 0 | 1 | 10 | 10 | 10 | N | 0 |
| E03 | 0 | 3 | 31 | 13 | 11 | 16 | Y | 0 |

TABLE 7

Control data information.
Zebrafish control library Roche 454
sequencing reads information

| | |
|---|---:|
| Number of sequence template | 38 |
| Total reads in analysis | 32453 |

TABLE 7-continued

Control data information.
Zebrafish control library Roche 454
sequencing reads information

| | |
|---|---:|
| Total unique sequences | 1776 |
| Total reads in top 38 sequences (percentage) | 28194 (87%) |

What is claimed is:

1. A method of identifying an antigen-specific antibody lineage in a subject exposed to the antigen, comprising,
   sequencing nucleic acid from a biological sample obtained from the subject after exposure to the antigen, via high throughput sequencing, to determine CDR3 nucleic acid sequences, representing at least a portion of the subject's antibody repertoire;
   performing a linkage analysis of the CDR3 nucleic acid sequences to establish linked CDR3 sequences, wherein two CDR3 sequences are in a linkage if they have the same V and J assignment and no more than one amino acid difference in the CDR3 region;
   grouping CDR3 sequences into a plurality of lineages, wherein individual lineages of the plurality comprise (i) identical CDR3 sequences and (ii) CDR3 sequences that are associated with one another through one or more linkages; and
   comparing the CDR3 sequences in the plurality of lineages with a CDR3 sequence of an antigen-specific antibody obtained from the subject to determine the presence of the antigen-specific antibody lineage.

2. The method of claim 1, wherein the antigen is a vaccine.

3. The method of claim 2, further comprising,
   (a) carrying out the method using a first biological sample obtained from the subject at a first time point;
   (b) carrying out the method using a second biological sample obtained from the subject at a second time point; and (c) comparing the lineage structure determined in (a) with the lineage structure determined in (b), wherein after the first time point and prior to the second time point the vaccine is administered to the subject.

4. The method of claim 1, further comprising quantitating the abundance of individual CDR3 amino acid sequences within individual lineages by counting the number of sequencing reads of the counterpart CDR3 nucleic acid sequences.

5. The method of claim 1, further comprising,
quantitating an average number of mutations within the individual lineages, wherein the average number of mutations is the average over a plurality of sequence reads of the CDR3 regions within the individual lineages.

6. The method of claim 1, wherein the biological sample is selected from the group consisting of blood, lymph, sputum, and tissue.

7. The method of claim 6, wherein the biological sample is blood.

8. The method of claim 1, further comprising quantitating sizes of the individual lineages by determining the number of linked CDR3 sequences in the individual lineages.

* * * * *